US011786625B2

(12) United States Patent
Liu et al.

(10) Patent No.: US 11,786,625 B2
(45) Date of Patent: Oct. 17, 2023

(54) AIR DECONTAMINATION AND SELF-RENEWING PURIFICATION SYSTEM UTILIZING A FILTER

(71) Applicant: Metalmark Innovations, PBC, Cambridge, MA (US)

(72) Inventors: Sissi Liu, Arlington, MA (US); Elijah Shirman, Winchester, MA (US); Tanya Shirman, Winchester, MA (US)

(73) Assignee: Metalmark Innovations PBC, Cambridge, MA (US)

( * ) Notice: Subject to any disclaimer, the term of this patent is extended or adjusted under 35 U.S.C. 154(b) by 0 days.

(21) Appl. No.: 17/709,069

(22) Filed: Mar. 30, 2022

(65) Prior Publication Data

US 2023/0001039 A1 Jan. 5, 2023

Related U.S. Application Data

(60) Provisional application No. 63/304,384, filed on Jan. 28, 2022, provisional application No. 63/271,326, (Continued)

(51) Int. Cl.
*A61L 9/16* (2006.01)
*A61L 9/20* (2006.01)
(Continued)

(52) U.S. Cl.
CPC ............... *A61L 9/16* (2013.01); *A61L 9/205* (2013.01); *B01D 39/1607* (2013.01);
(Continued)

(58) Field of Classification Search
CPC .................. A61L 9/16; B01D 46/785
See application file for complete search history.

(56) References Cited

U.S. PATENT DOCUMENTS 5,364,586 A 11/1994 Trusov et al.
6,359,374 B1 3/2002 Dausch et al.
(Continued)

FOREIGN PATENT DOCUMENTS

EP 1704909 A2 9/2006
WO 0020106 A2 4/2000
(Continued)

OTHER PUBLICATIONS

International Search Report and Written Opinion, PCT/US2022/035854, dated Oct. 18, 2022, 15 pages.
(Continued)

*Primary Examiner* — Kevin Joyner
(74) *Attorney, Agent, or Firm* — Potomac Law Group, PLLC

(57) ABSTRACT

An air purification system includes a conduit extending between an inlet and an outlet, each in fluid communication with an enclosed environment. Ambient air from the enclosed environment enters the conduit via the inlet and treated air exits the conduit and enters the enclosed environment via the outlet. The system further includes a fibrous filter disposed within the conduit and configured to treat the ambient air thereby generating the treated air, and a renewal unit disposed within the conduit and configured to renew the fibrous filter.

57 Claims, 13 Drawing Sheets

Related U.S. Application Data filed on Oct. 25, 2021, provisional application No. 63/216,897, filed on Jun. 30, 2021.

(51) Int. Cl.
*B01D 46/66* (2022.01)
*B01D 39/16* (2006.01)
*B01D 39/20* (2006.01)
*B01D 46/00* (2022.01)

(52) U.S. Cl.
CPC ..... *B01D 39/2041* (2013.01); *B01D 46/0028* (2013.01); *B01D 46/0036* (2013.01); *B01D 46/785* (2022.01); *A61L 2209/111* (2013.01); *A61L 2209/12* (2013.01); *A61L 2209/14* (2013.01); *A61L 2209/21* (2013.01); *A61L 2209/22* (2013.01); *B01D 2239/0442* (2013.01); *B01D 2239/0492* (2013.01); *B01D 2273/30* (2013.01); *B01D 2279/50* (2013.01); *B01D 2279/65* (2013.01)

(56) References Cited

U.S. PATENT DOCUMENTS

| | | | | |
|---|---|---|---|---|
| 2005/0211415 | A1* | 9/2005 | Arts | F24F 1/04 165/59 |
| 2006/0127288 | A1* | 6/2006 | Hay | A61L 9/014 422/186.3 |
| 2006/0286921 | A1* | 12/2006 | Arts | F24F 8/108 454/187 |
| 2009/0010801 | A1 | 1/2009 | Murphy et al. | |
| 2009/0049639 | A1* | 2/2009 | Gordon | A47L 9/32 15/319 |
| 2018/0141119 | A1 | 5/2018 | Shu et al. | |
| 2018/0272024 | A1* | 9/2018 | Seo | B01D 53/8668 |
| 2020/0030731 | A1 | 1/2020 | Dhau et al. | |
| 2021/0205803 | A1 | 7/2021 | Shirman et al. | |

FOREIGN PATENT DOCUMENTS

| | | |
|---|---|---|
| WO | 2014210608 A1 | 12/2014 |
| WO | 2016115451 A1 | 7/2016 |
| WO | 2016183237 A1 | 11/2016 |
| WO | 2018078587 A1 | 5/2018 |
| WO | 2019068110 A1 | 4/2019 |

OTHER PUBLICATIONS

International Preliminary Report on Patentability, PCT/US2021/012271, dated Jul. 21, 2022, 9 Pages.
International Preliminary Report on Patentability, PCT/US2021/037454, dated Dec. 29, 2022, 10 Pages.
International Search Report and Written opinion for International Application No. PCT/US2021/037454, dated Oct. 15, 2021.
International Search Report and Written Opinion, PCT/US2021/012271, dated Apr. 26, 2021, pp. 11.
Vijayaragavan, "Virus Purification, Detection and Removal", Michigan Technological University, Jan. 1, 2014.

* cited by examiner

AIR DECONTAMINATION AND SELF-RENEWING PURIFICATION SYSTEM UTILIZING A FILTER

RELATED APPLICATIONS

The present application claims priority to a provisional application entitled Air Decontamination and Purification System Utilizing Reaction Device having application No. 63/216,897 filed on Jun. 30, 2021, claims priority to a provisional application entitled Air Decontamination and Purification System Utilizing Reaction Device having application No. 63/271,326 filed on Oct. 25, 2021, and claims priority to a provisional application entitled Air Decontamination and Purification System having application No. 63/304,384 filed on Jan. 28, 2022, all of which are incorporated by reference entirely herein.

FEDERALLY SPONSORED RESEARCH

This invention was made with government support under contract 2026128 awarded by the National Science Foundation. The government has certain rights in the invention.

TECHNICAL FIELD

The present disclosure relates to an indoor, e.g., in-building, in-cabin, or outdoor air purification system, and particularly to such a system for treating the air, e.g., for efficient inactivation of viruses, and other pathogenic microorganisms, and removal of gaseous or particulate contaminants.

BACKGROUND

There are many indoor air purification devices currently on the market. Some emerging technologies for outdoor air quality improvement have also been introduced. Such technologies can include 1) mechanical filters (e.g., fibrous, metallic, and ceramic filters) that mechanically trap airborne contaminants within the filter; 2) sorption filters (e.g., filters including activated carbon) that remove certain gaseous molecules or odors from the air by physically or chemically binding airborne molecules to the sorbent; 3) electrostatic filters that electrically charge airborne contaminants as they enter the filter, causing these contaminants to become attracted to and trapped within the filter; and 4) photocatalytic filters that are commonly used in combination with UV light to degrade airborne contaminants. In practice, all of these filters have various shortcomings. For example, HEPA filters, though they exhibit high efficiency as particle filters, are ineffective for treating volatile organic compounds (VOCs). Further, many traditional air purification systems have a tendency to release trapped contaminants or even generate hazardous by-products. Most applications require high maintenance time and frequent filter media replacements.

Accordingly, there is a need for improved air purification devices, which can be efficiently employed in a variety of environments, such as buildings, aircrafts, vehicles, outdoors, etc.

SUMMARY

In one aspect, an air purification system is disclosed, which includes a conduit extending from an inlet through which a flow of ambient air may be received to an outlet through which treated air can exit the conduit. In some embodiments, a device for facilitating air circulation, e.g., a fan, can be used to facilitate the flow of the air through the conduit. A filter is disposed within the conduit to treat the incoming air. In some embodiments, the filter has a primary porous filtration unit and a secondary porous structure that can modulate the filtration functionality of the primary porous filtration unit. The treated air exits the conduit via its outlet. A renewal unit, e.g., a heating element, can also be positioned in the conduit such that it can be intermittently activated, e.g., it can be activated according to a predefined schedule, such as daily, weekly, monthly, or otherwise, so as to treat contaminants captured, or otherwise treated, by the filter, thereby renewing the filter. For example, the renewal unit can renew the filter, via heat, light, magnetic field, infrared radiation, or any other suitable energy modality. In some embodiments, heat may be used to renew the filter. In these embodiments, heat may be transferred from the renewal unit to the filter conductively or convectively.

In a related aspect, an air purification system is disclosed, which comprises a conduit having an air inlet conduit portion having an inlet for receiving ambient air, renewal loop in which a filter (e.g., a fibrous filter) is positioned, and an air outlet through which the treated air exits the conduit.

In some embodiments, the air purification system can include a primary conduit, which extends from an inlet to an outlet and in which a filter is positioned, and a secondary conduit that is coupled to the primary conduit and is fluidly coupled at two fluid connections to the primary conduit, where one of the fluid connections (herein also referred to as the upstream connection) is positioned upstream of the filter and the other fluid connection (herein referred to as the downstream connection) is positioned downstream of the filter. A fluid connection allows a liquid or gas (e.g., air) to flow between the primary and secondary conduits. In some such embodiments, one valve (herein referred to as the upstream valve) is coupled to the upstream fluid connection and another valve (herein referred to as the downstream valve) is operably coupled to the downstream fluid connection with the filter positioned between the two valves. In some embodiments, a treatment unit is positioned within the secondary conduit. The treatment unit may have the same structure as the filter or a different structure. By way of example, the treatment unit may be a sorption filter, a catalytic filter or a combination thereof.

In some embodiments, the filter can include a primary porous structure. The primary porous structure provides a filtration functionality that allows the filter to treat an incoming airflow containing contaminants. In some embodiments, the primary porous structure captures at least 1% or more of contaminants (e.g., at least 5%, or at least 10%, or at least 20% at least 30%, or at least 40%, or at least 50%, or at least 60%, or at least 70%, or at least 80%, or at least 90%, or at least 95%, or at least 99%, or at least 99.9%, or at least 99.97%, or at least 99.99%, or at least 99.999%, or more of contaminants), measured based on the filter's most penetrating particle size (MPPS) in the incoming air flow.

In some embodiments, the filter includes a porous macroscopic substrate that includes a plurality of interconnected passages.

In some embodiments, a primary porous structure or a porous macroscopic substrate have pore sizes in a range of about 10 nm to about 3 mm.

In some embodiments, the filter can be made of fibrous media e.g., non-woven and/or woven fibrous media. In some such embodiments, the fibers of the filter are layered into a web which is then bound together by pressure, chemical, mechanical, heat or solvent treatment, and/or by the interlocking of fibers. An example of a fibrous medium is fiberglass.

In some embodiments, the filter can include a high efficiency particulate air (HEPA) filter or ultra-low particulate air (ULPA) filter In some embodiments, the filter can be made of, include, or be coated with any of fiberglass, polymer fibers, natural fibers such as cotton or silk, other synthetic materials such as cellulose acetate, cellulose nitrate (collodion), polyamide (nylon), polycarbonate, polypropylene, and polytetrafluoroethylene, stainless steel, aluminum, galvanized steel, nickel alloy, Inconel, FeCrAl alloy, silicon dioxide, other metal oxides or a combination thereof.

As used herein, a fibrous filter includes any woven or nonwoven and a combination of non-woven and woven fiber-based materials.

In some embodiments, the filter can include or can be coated with a reactive medium providing different functions, e.g., for inactivation of pathogens and decomposition of organic and inorganic gaseous contaminants. The surface of the reactive medium may exhibit a composition and/or a morphology configured to facilitate the entrapment or deactivation of said at least one contaminant (e.g., particulate, pathogen). Such a coating can be, for example, in the form of a continuous or discontinuous thin coating of a non-porous material, such as those disclosed herein.

In some embodiments, the reactive medium can include organic materials (e.g., enzymes), or inorganic materials (e.g., metals, metal oxides such as silver, copper oxide, manganese oxide).

In some embodiments, the reactive medium can include sorption materials (e.g., activated carbon, zeolites, etc.) In other embodiments, the reactive medium can include metals (e.g., gold, silver, copper, etc.). In further embodiments, the reactive medium can include catalytic materials. In some embodiments, the catalytic material may include metal nanoparticles, such as gold, silver, platinum, palladium, ruthenium, rhodium, cobalt, iron, nickel, osmium, iridium, rhenium, copper, chromium, tungsten, molybdenum, vanadium, niobium, tantalum, titanium, zirconium, hafnium, bimetals, metal alloys, metal compounds, such as pnictides, hydroxides, binary and complex salts, including heteropoly acids and their derivatives or a combination thereof.

In some embodiments, the reactive medium includes a continuous film. In other embodiments, the reactive medium includes a plurality of discontinuous surface segments. Yet, in other embodiments, the reactive medium can comprise a plurality of nanoparticles distributed within at least some portions of the filter. Such functional nanoparticles can have a size in a range of about 0.5 nm to about 500 nm. The overall system design can result in enhanced efficiency towards inactivation of pathogenic organisms and removal of gaseous contaminants or particulates.

In some embodiments, the nanoparticles are composed of metals or metal oxides. In some embodiments, the nanoparticles include polymeric compounds of synthetic or natural origin or combination of thereof such as Polystyrene, polyamin, a protein- or polysaccharide-based material, silk fibroin, chitin, shellac, cellulose, chitosan, alginate, gelatin. In some embodiments, the nanoparticles can include catalytic nanoparticles. In some embodiments, the reactive medium can alter the surface chemistry of the filter through, for example, modification with chemical functional groups such as amine, thiol or quaternary ammonium salts. In some embodiments, the reactive medium can add a sorption function. In some embodiments, the function of the reactive medium can result from its composition, morphology or combination of both.

In some embodiments, the reactive medium may modulate the filtration capability of the filter and may modulate the ability to renew the filter. The secondary reactive medium may not significantly increase (and in some cases may not increase) a back pressure i.e., a pressure differential across the inlet and outlet of the filter (e.g., below 50× increase, or below 10× increase, or below 5× increase, or below 1× increase, or below 0.5× increase, or less or no change in the back pressure) relative to a similar filter without the secondary porous coating operating under similar flow conditions (e.g., in the range of 0.1 to 10,000 cubic feet per minute (CFM), or 0.5 to 1000 CFM, or 1 to 500 CFM, e.g., 200 or 400 CFM).

In some embodiments, the filter may include a primary porous structure and a secondary porous structure (e.g., a porous coating) that is coupled to the primary porous structure. In some embodiments, the pores of the secondary porous structure exhibit a geometry, a surface morphology and/or a size configured to facilitate the entrapment or deactivation of said at least one contaminant (e.g., particulate, pathogen). In some embodiments, the secondary porous structure includes a continuous film. In other embodiments, the secondary porous structure includes a plurality of discontinuous surface segments. Yet, in other embodiments, the secondary porous structure comprises a plurality of porous functional particles distributed within at least some portions of the filter. The size of particles can be in a range of about 0.5 μm to about 30 μm.

In some embodiments, the pores of the coating exhibit a cross-sectional dimension in a range of about 1 nm to about 10 microns, e.g., in a range of about 10 nm to about 10 microns, about 80 nm to about 5 microns, about 100 nm to about 5 microns, about 200 nm to about 5 microns, about 250 to about 5 microns, about 300 nm to about 2 microns, about 500 nm to about 2 microns, or in a range or about 1 to about 2 microns. In some embodiments, the pores of the secondary coating exhibit a geometry, a surface roughness and/or a size configured to facilitate the entrapment of said at least one contaminant (e.g., particulate).

In some embodiments, the secondary porous structure can be composed of ceramic, metal, metal oxide, mixed metal oxides, polymeric material, biogenic material or any combination thereof, and others.

In some embodiments, the secondary porous structure may modulate the filtration capability of the filter and may modulate the ability to renew the filter. The secondary porous structure may not significantly increase (and in some cases may not increase) a back pressure i.e., a pressure differential across the inlet and outlet of the filter (e.g., below 50× increase, or below 10× increase, or below 5× increase, or below 1× increase, or below 0.5× increase, or less or no change in the back pressure) relative to a similar filter without the secondary porous coating operating under similar flow conditions (e.g., in the range of 0.1 to 10,000 cubic feet per minute (CFM), or 0.5 to 1000 CFM, or 1 to 500 CFM, e.g. 400 or 200 CFM).

In some embodiments, the secondary porous structure (e.g., a porous coating) can include a reactive medium distributed on the surface of the coating and/or throughout at least some of the pores. In some embodiments, the reactive medium can include organic materials (e.g., enzymes), and/or inorganic materials (e.g., metals, metal oxides such as silver, copper oxide, manganese oxide).

In some embodiments, the reactive medium can include sorption materials (e.g., activated carbon, zeolites, etc.) In other embodiments, the reactive medium can include metals (e.g., gold, silver, copper, etc.). In further embodiments, the reactive medium can include catalytic materials.

In some embodiments, the reactive medium can comprise a plurality of nanoparticles distributed within at least some portions of the secondary porous structure. The nanoparticles can be about 0.5 nm to about 500 nm in size. In some embodiments, the nanoparticles are composed of metals or metal oxides. In some embodiments, the nanoparticles include organic compounds. In some embodiments, the reactive medium can alter the surface chemistry of the secondary porous coating.

In some embodiments, the reactive medium can add a sorption function. In some embodiments, the reactive medium can form a homogeneous coating or discrete particles on the surface of secondary structure. In some embodiments, the function of the reactive medium can result from its composition, morphology or combination of both.

Further, in some embodiments, the present teachings can help preserve the mechanical integrity of a filter through various mechanisms, e.g., preventing shedding or improving dissipation of stresses that can lead to the formation of microcracks.

In some embodiments, the application of the reactive medium on the filter or coating of the filter with a secondary porous structure results in functionalized filter in which these coatings provides additional functions to the filter and can result in enhanced efficiency towards inactivation of pathogenic organisms and removal of gaseous contaminants or particulates.

In many embodiments, the inclusion of a secondary porous coating with reactive medium on one or more interior surfaces of the filter without blocking the passages or pores can provide a functionalized filter that operates effectively with a relatively small increase in back pressure relative to a similar filter without the coating. In other words, a functionalized filter can treat at least some contaminants (e.g., pathogens such as viruses, particulate matter, or gaseous contaminants) in the air, without significantly restricting the passage of air through the system. In this regard, the back pressure of a functionalized filter for a desired range of air flow rate can remain within an acceptable range, e.g., within about 50× of the back pressure of the uncoated filter. By way of example, the incremental back pressure can be within about 50×, or about 40×, or about 30×, or about 20×, or about 10×, or about 5×, or about 1×, or about 0.5×, or less or no change.

The air purification system can further include a renewal unit for at least intermittently treating a filter, e.g., so as to inactivate, at least partially decompose, or at least partially remove contaminants, such as pathogen particles, captured by the filter via, e.g., heating, exposure to light, magnetic field, electromagnetic field, ionization, etc. applied at certain time intervals or based on environmental triggering. By way of example, the environmental triggering for the initiation of filter renewal can be based on the detection of a sudden increase or an increase above a threshold value in the concentration of contaminants in the ambient air, in the back pressure across the filter, or room occupancy.

The renewal unit can be configured to apply heat and/or electromagnetic radiation (e.g., microwave radiation), visible light, UV (ultraviolet), infrared, or another type of energy (e.g., plasma) to the air passing through a filter (i.e., a filter used during operation of the air purification device to treat (filter) the incoming air) and/or directly to the filter itself so as to cause the release of at least a portion of the contaminants entrapped the filter. By way of another example, in some embodiments, a burst of pressurized air can be applied to the filter to dislodge at least a portion of contaminants captured by the filter. In this example, the burst of pressurized air is applied to the filter in a direction that is opposite to the direction of the flow of the air to be filtered.

A variety of energy sources (e.g., heat, light sources) can be employed within the renewal unit in practice of the present teachings. Some examples of suitable energy sources can include, without limitation, at least one of a bobbin heater, a heating coil, a heat tape, an inductive coil, a flame, or sources of electromagnetic emission, e.g., in the form of light (e.g., microwave radiation, infrared radiation or UV radiation), or magnetic field or a combination thereof.

In some embodiments, the thermal energy can be transferred from the renewal unit to the filter conductively or convectively. For example, the renewal unit can include a heat source in direct contact with the filter or a fluid medium (e.g., air) that transfers the energy from the heat source to the filter, respectively.

In some embodiments, the energy source can be configured to raise the temperature of incoming air to a value in the range of about 20° C. to about 750° C., e.g., about 50° C. to about 400° C., or about 60° C. to about 300° C. In some embodiments, the energy source can include a heat exchanger or other heat recovery device.

In some such embodiments, a renewal unit can be positioned within the primary or the secondary conduit, where the renewal unit can be activated intermittently, e.g., according to a predetermined schedule, to renew the filter or start, stop, or modulate treatment unit operations.

In some embodiments, a controller can control the renewal process, e.g., via activation and inactivation of a heater and/or adjusting the heating level provided by the heater, according to predefined criteria. By way of example, the controller can be programmed to activate the heater to heat the air flowing through the filter. A temperature sensor in communication with the controller may be used to monitor the temperature of the heated air as it is being heated by the heater. In response to signals from the temperature sensor, the controller can adjust the heater to ensure that the air temperature remains within an elevated range that is suitable for achieving renewal of the filter, e.g., in a range of about 50° C. to about 100° C. or to about 150° C., or 200° C., or 250° C., or 300° C. In some embodiments wherein the filter is tolerant to higher temperatures, e.g., high temperature HEPA filter, the temperature may be elevated to a range of about 450° C. to 500° C.

In some embodiments, the system may be divided into multiple parts, such that each part is renewed in a different period of time. For example, the system may include multiple renewal units, such as multiple heaters, for renewing different sections of one or more of the filters. The controller may turn on the different renewal units at different times and therefore renew the different sections of the filter at different times. Such a division of the renewal time may be employed, for example, when a full renewal operation of the whole system requires many resources such as electricity that may not be available; or when a full renewal may take longer than acceptable for the system to halt its air purification operation. In the latter case, the multiple periods of renewal may be staggered among multiple periods of air purification operation.

In some cases, the upstream and the downstream valves can each be moved between a first position and a second position. In the first position, the valves allow air to only pass through the primary conduit. Stated another way, in the first position, the valves inhibit air from flowing into the secondary conduit. In the second position, the valves inhibit the flow of the air into and out of the section of the primary conduit that is positioned between the upstream and the downstream valves, and further open the upstream and the downstream fluidic connections such that the combination of a portion of the primary conduit that is positioned between the valves and the secondary conduit forms an air flow loop (herein also referred to as a "renewal loop"). Before or after the renewal loop is established, the renewal unit can be activated for renewing the filter so as to reduce, and preferably eliminate contaminants adsorbed, trapped or otherwise retained by the filter. Subsequently, the upstream and the downstream valves can be returned to a state (the first position) in which they allow the ingress of the ambient air into the primary conduit via its inlet to be treated by the filter and further allow the egress of the treated air out of the conduit through its outlet. In some embodiments, the valves may be moved to any number of positions between the first and second positions. These positions modulate an air flow within the primary and/or secondary conduit. In other embodiments, one of the downstream valves may be moved to the second position while the upstream valve is in the first position thereby allowing ambient air to enter the conduits during a renewal cycle.

Another filter or a treatment unit positioned downstream or upstream of the filter can treat (e.g., deactivate, decompose, or otherwise eliminate) at least a portion of the contaminants released from the filter during a renewal period before releasing the air stream through the outlet to the external environment.

In some embodiments, the air purification system can further include a fan disposed upstream or downstream of the air inlet for facilitating air flow through the system. In some embodiments, a conduit in which a filter is positioned can have a substantially linear configuration. Such a conduit, or any other conduit of an air purification device, can have a variety of different cross-sectional profiles, such as circular, square, rectangular, etc.

The system can further include one or more heat transfer elements that are positioned along a path of air flow to increase thermal contact with the flowing air and configured to improve heat dissipation and/or absorption efficiency.

Further, in some embodiments, the system can include multiple filters, e.g., connected in series or in parallel, or a combination of series and parallel connections.

The device can be used for air purification or in other applications involving filtration such as a Diesel Particulate Filter (DPF), gas filtration membrane, and liquid filtration membrane.

DETAILED DESCRIPTION

Figure 1A:
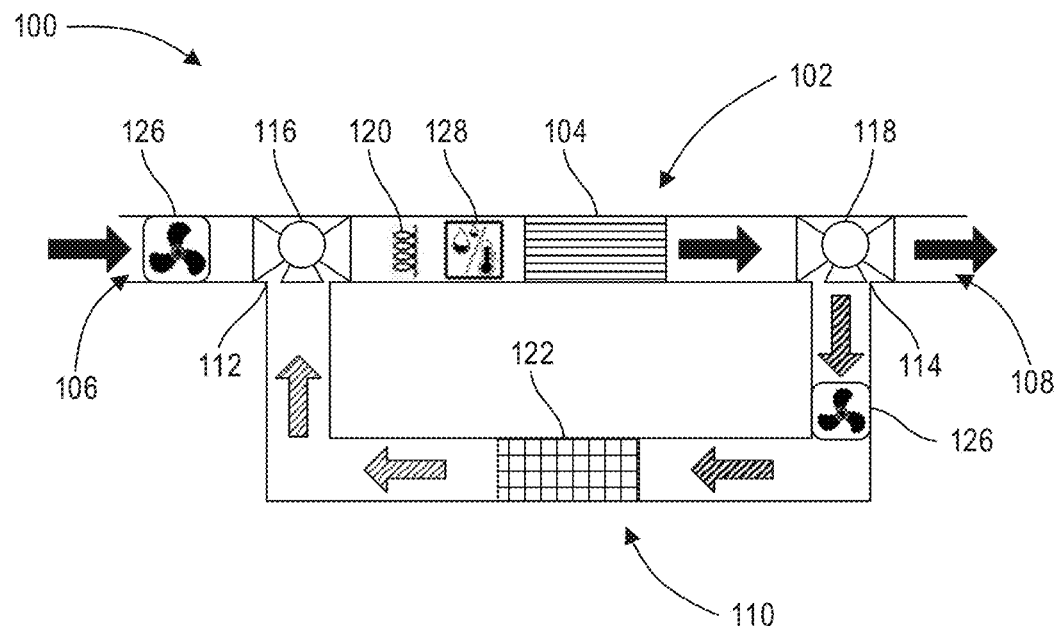
FIGS. 1A-1J are schematic representations of various double conduit air purification systems according to various exemplary embodiments.
Figure 1B:
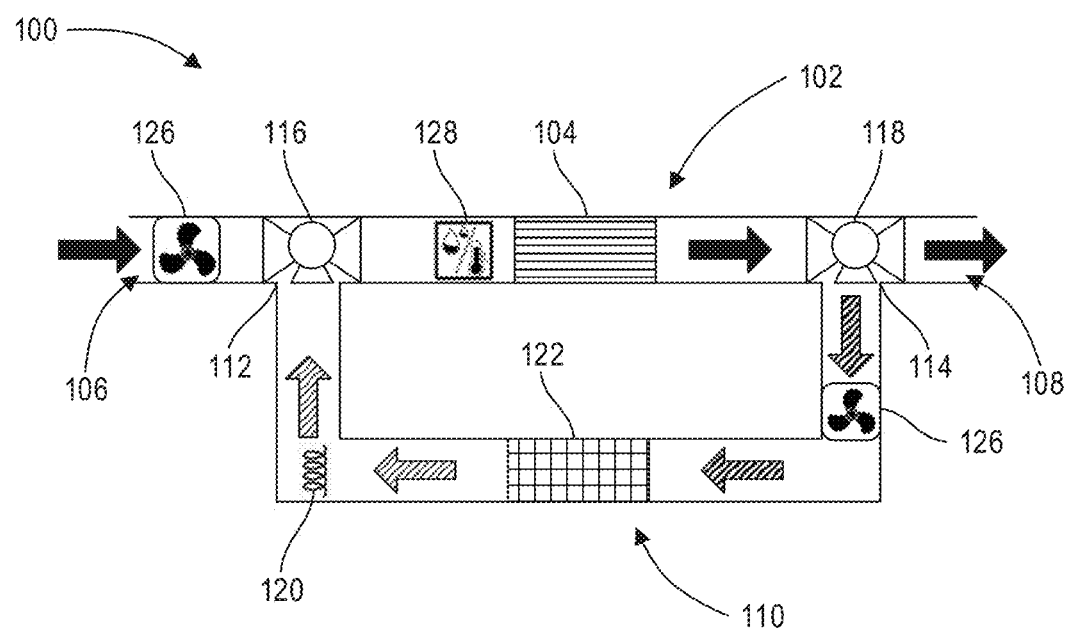
Figure 1C:
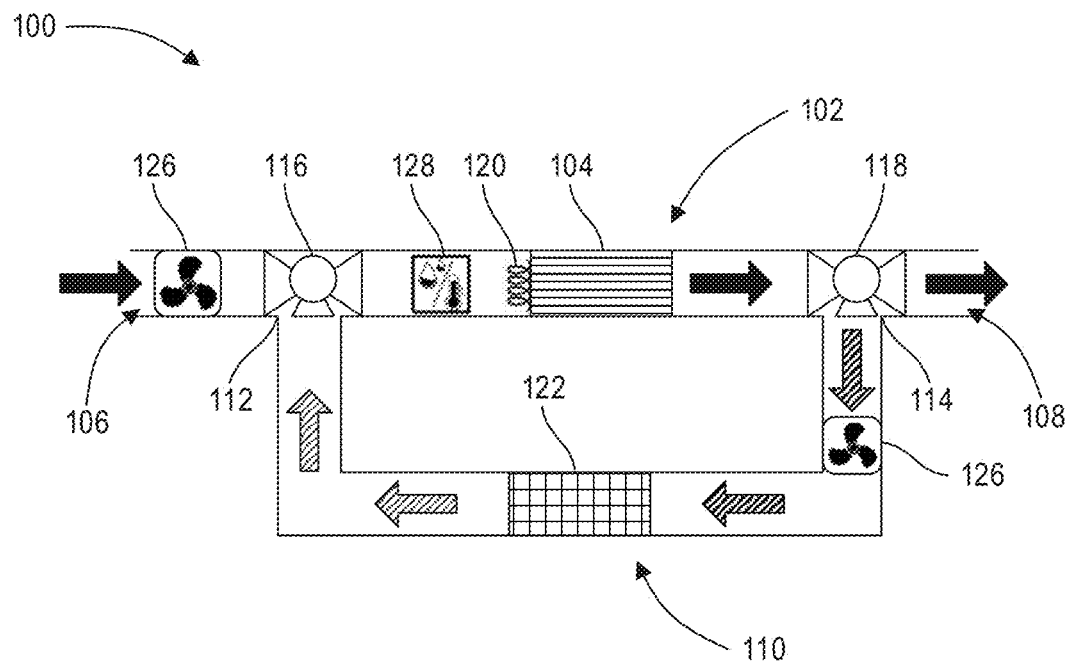

Further understanding of various aspects of the present teachings can be found in the following description in conjunction with the associated drawings, which are described briefly below.

The term "filter," as used herein, refers to a device that removes a contaminant from the air by retaining and/or eliminating the contaminant. Filters include, but are not limited to, high efficiency particulate air (HEPA) filters, ultra-low penetration air (ULPA) filters, mechanical filters, sorption filters, ionization and electrostatic filters, and photocatalytic filters. A filter may include a reactive medium for inactivation of pathogens and/or decomposition of particulates. In some embodiments, a filter as described herein may also include a macroscopic porous substrate having primary porous structures that can provide filtration even in the absence of a secondary porous structure coupled to the primary porous structure. In further embodiments, the filter may include a primary porous structure and a secondary porous structure that modulates a treatment capability of the filter.

The terms "fibrous filters" and "fiber filter medium" are used herein interchangeably to refer to a filter/filter medium comprising non-woven and/or woven fibrous media (e.g., fiberglass). Fibers of a fibrous filter can be layered into a web which is then bound together by chemical, pressure, mechanical, heat or solvent treatment, and/or by the interlocking of fibers.

In some embodiments, the filter can be made of woven fibrous media where fibers overlap one another.

A "sorption filter" includes a sorption material (e.g., activated carbon, charcoal, zeolites, metal oxides, or the like).

Although various aspects of the present teachings are described herein in connection with filtration of air, it should be understood that the filters disclosed herein can also be employed for filtration of the fluids, such as a variety of liquids.

As used herein a "functionalized filter" refers to a filter having a primary porous structure coated with reactive medium or functionalized with a secondary porous structure (e.g., a porous coating) that provides additional functions to the filter (e.g., improved filtration, facilitated renewal function, sorption, introduction of antimicrobial function or catalytic function to decompose gaseous pollutants, etc.). The secondary porous structure can include a continuous film, a plurality of discontinuous surface segments and/or a plurality of porous functional particles distributed within at least some portions of the filter. The secondary porous structure can have pore sizes in a range 1 nm to 10 microns and the size of porous functional particles can be in a range of 0.5 µm to 30 µm. In some embodiments, a reactive medium is distributed throughout within at least some of the pores of the filter or can be applied to the secondary porous coating. The reactive medium can include, but is not limited to, biocatalysts (e.g., enzymes), platinum group metals (e.g., platinum, palladium, rhodium, iridium), gold, silver, copper, metal oxides (e.g., copper oxide, silver oxide, magnesium oxide), sorption material (e.g., activated carbon, zeolites, etc.) or any combinations thereof. The reactive medium can include a continuous film, a plurality of discontinuous surface segments and/or a plurality of nanoparticles distributed within at least some portions of the filter or secondary porous structure. The nanoparticles can have size ranging from about 0.5 nm to about 500 nm in at least one dimension and in some cases all dimensions.

The present disclosure is directed to filters that can be used for filtration of a fluid. In some embodiments, such a filter can include a macroscopic porous structure and a reactive medium that is coupled to the macroscopic porous structure. While in some embodiments, the reactive medium is non-porous, in other embodiments it can be porous. In some embodiments, a secondary porous structure is coupled to the macroscopic porous structure. In some such embodiments, a reactive medium can be coupled to the secondary porous structure. The reactive medium and the secondary porous structure can modulate the filtration characteristics (e.g., filtration efficiency) of the macroscopic porous structure and/or modulate the ability to renew the filter, e.g., via application of heat and/or electromagnetic radiation to the fluid and/or directly to the filter.

A reactive medium may inactivate and decompose organic contaminants and gaseous contaminants within air flowing through the filter. In some embodiments, a reactive medium can include organic materials (e.g., enzymes) or inorganic materials (e.g., metals, metal oxides such as silver, copper oxide, manganese oxide). In other embodiments, a reactive medium can include sorption materials (e.g., activated carbon, zeolites, etc.), or catalytic particles.

The term "contaminants" and "pollutants" are herein used interchangeably to refer to a variety of inorganic, organic, and mixed inorganic and organic material structures, including naturally-occurring or artificial material structures, such as a variety of microorganisms (e.g., bacteria and/or viruses), smoke, or other types of particulates. Contaminants can encompass particulates of organic, inorganic and mixed origin, aerosols including bioaerosols, and gaseous contaminants such as volatile organic compounds (VOCs). In general, contaminants may include different types of particulates, chemicals, or organisms that may accumulate in the filter during its use and deteriorate the performance of the filter. The deterioration may include a reduction in the rate at which the filter can treat the air, the quantity or type of the contaminants that the filter can capture in a unit of time, or the increase in backpressure of the filter that would render the overall system inefficient or inoperable for the intended use.

By way of example, particulates can have a size of about 10 microns or below (e.g., "PM10"), or about 2.5 microns or below (e.g., "PM2.5"), or about 1 micron or below (e.g., "PM1"), or about 300 nm or below. The term "ultrafine particulate," typically refers to a particle having a size of about 0.1 microns ("PM0.1") or below.

Bioaerosols can include bacteria, viruses, fungi, algae, dust mites, or others. In addition, biological materials such as pollen, endotoxins, proteins, and animal excreta form aerosols. Airborne pathogens are almost always embedded in droplets along with various levels and types of organic and inorganic materials. This heterogeneity represents a significant challenge and needs to be taken into account in the development and evaluation of air decontamination technologies.

The terms "renew" and "regenerate" and their derivatives are used herein interchangeably. In particular, renewal of a filter may mean the process of improving the functionality of the filter after the functionality has deteriorated due to being used for a period of time. The deterioration of the functionality may result, for example, from accumulation of contaminants in the filter. The renewal of the filter may include, for example, removing some or all of the accumulated contaminants from the filter. The renewal of the filter may include bringing the state of the filter substantially back to a state in which the filter is capable of performing its intended function. Air purification systems disclosed herein may renew or regenerate fibrous filters. As will be discussed in further detail, renewing a filter may include heating the filter to a threshold temperature. Applicants have surprisingly found that fibrous filters may be incorporated in air purification systems in which a regeneration system is utilized to regenerate/renew the fibrous filters. As such, air purification systems disclosed herein provide an improvement over existing air purification systems as the disclosed air purification systems are able to renew fibrous filters as well as non-fibrous filters. In some embodiments, the renewal process also aids in the effective inactivation of pathogens (e.g., viruses, bacteria, fungi, etc.), trapped by the filter.

The terms "treat" and "treatment" are used herein to refer to oxidation, reduction, inactivation, degradation, filtration, entrapment, or sorption (e.g., removal, breakdown) (or a combination thereof) of a contaminant (e.g., gas, vapor, particulate matter, aerosol, bioaerosol, or pathogen) from a medium (e.g., a gas or liquid medium), including a flowing medium, e.g., in the form of a polluted stream.

The term "entrapment," as used herein, refers to a permanent or temporary capture (e.g., filtration, sorption, etc.) of a contaminant by a structure or chemical according to the present teachings.

The terms "pore," "passage," "passageway," and "channel" are herein used interchangeably to refer to a material structure having at least one opening for receiving a flow of medium (e.g., an air flow). The pores can be of a spherical or non-spherical shape, e.g., linear, curvilinear, tortuous, bifurcating, or branched cavity that can provide an enclosure or a surface that is exposed to the flow. In some embodiments the term pore relates to a space between a plurality of interleaving fibers (e.g., a set of woven or nonwoven fibers) of the primary porous structure.

The term "back pressure" is used herein to refer to a pressure drop or loss in a flow of a medium across the material structure, e.g., between an inlet and an outlet of a filter.

The term "size" as used herein refers to a cross-sectional dimension, e.g., a dimension, such as a maximum dimension, perpendicular to an elongated dimension (e.g., length) of a pore or a channel (such as a diameter of a pore or a channel), e.g., in the case of a high aspect ratio pore (when the ratio between the long and the short dimension of a pore is greater than 1.5). As such, in the embodiments discussed below, a pore or a channel can be characterized by one or more of its cross-sectional dimensions and its length.

The term "nanoparticle" refers to a material structure having a size in each of the x-, y- and z-dimension that is less than 1 micron, e.g., in a range of about 0.5 nm to about 10 nm, in a range of about 5 nm to about 30 nm, in a range of about 30 nm to about 100 nm, or in a range of about 100 nm to about 500 nm.

As used herein, a "valve" refers to a device for controlling fluid (e.g., air, liquid, etc.) passage through a conduit. Valves include, but are not limited to two-way valves, three-way valves, etc.

As used herein, the term "about" means plus or minus 10% of the numerical value of the number with which it is being used. Therefore, about 100 μm means in the range of 90 μm-110 μm.

FIGS. 1A-1J schematically depicts an air purification system 100 with a renewal/regeneration loop in accordance with an exemplary embodiment. The air purification system 100 may be used outdoors or indoors (e.g., in a building, a vehicle cabin, an aircraft cabin, or other enclosed environments).

The air purification system 100 includes a primary conduit 102 and a filter 104 disposed within the primary conduit 102. The primary conduit 102 extends between an inlet 106 and an outlet 108. In some embodiments, the filter 104 is configured to treat contaminant stream, e.g., to inactivate, reduce, and preferably remove contaminants, such as particulates, pathogens, and gaseous contaminants, e.g., volatile organic compounds (VOCs), from the air flowing through the filter via sorption, or catalytic processes, e.g., such as oxidation, or reduction. In some embodiments, the filter 104 may be a functionalized filter.

During operation of the air purification system 100, ambient air that enters the air purification system 100 via the inlet 106, is treated by the filter 104 thereby generating "treated air" and the treated air exits the air purification system 100 via the outlet 108.

The air purification system 100 further includes a secondary conduit 110 that is coupled to and is in fluid communication with the primary conduit 102. The secondary conduit 110 is coupled to the primary conduit 102 at a first connection (junction) 112 and at a second connection (junction) 114. As depicted in FIGS. 1A-1I, the first connection 112 is positioned upstream from the filter 104 and the second connection (junction) 114 is downstream from the filter 104.

The air purification system 100 further includes a first valve 116 and a second valve 118 operably coupled to the first and the second junctions 112 and 114, respectively. In some embodiments, each of the valves 116 and 118 can be implemented as a one way or a 2-way valve. In some embodiments, the valves 116 and 118 can be equipped with electromechanical actuators, thereby allowing an automated operation of the valves 116 and 118.

The first valve 116 is coupled to the primary conduit 102 and the secondary conduit 110 at the first junction 112 and the second valve is coupled to the primary conduit 102 and the secondary conduit 110 at the second junction 114. As such, the first valve 116 and the second valve 118 regulate the flow of air through the primary conduit 102 and the secondary conduit 110. The first valve 116 and the second valve 118 are each moveable between a first position and a second position. When the valves 116 and 118 are in the first position, air only flows through the primary conduit. Stated another way, in the first position the valves 116 and 118 inhibit air from flowing into the secondary conduit 110. In the second position the valve 116 blocks fluid communication between the inlet 106 and the remainder of the system 100. Further, when in the second position, the valve 118 blocks fluid communication between the remainder of the system and the outlet 108. In this position, the valves 116 and 118 allow fluid communication between a portion of the primary conduit 102 that is between the valves 116 and 118 and the secondary conduit 110, therefore defining a closed air circulation loop (which is also referred to herein as a "renewal loop"). During a renewal process, the valves 116 and 118 are placed in the second position and air may flow within the renewal loop. Subsequently, the valves 116 and 118 can be returned to the first position which allows the ingress of ambient air into the primary conduit 102 via the inlet 106 to be treated by filter 104 and further allow the egress of the treated air out of the primary conduit 102 via the outlet 108.

As contaminants are arrested on the filter 104, over time, the effectiveness of the filter 104 may gradually diminish, the pressure differential across the filter 104 may increase (e.g., due to pore clogging, material saturation) to levels that exceed safe system limits, and the trapped contaminants may be re-released to the outgoing air stream, thus releasing hazardous by-products into the environment through the treated air. Furthermore, as the filter 104 becomes clogged, a back pressure across the filter increases which may stress a motor that operates the air purification system 100 and cause its overheating. The additional stress placed on this motor may cause the motor to overheat which damages the motor. Accordingly, intermittent renewal of the filter 104 may be needed to eliminate and/or remove trapped contaminants from the filter 104.

The air purification system 100 includes a renewal unit 120 and a treatment unit 122 disposed within the secondary conduit 110. The treatment unit 120 may have the same structure as the filter 104 or a different structure. By way of example, the treatment unit may be a sorption filter, a catalytic filter or a combination thereof. During a "renewal process" the first valve 116 and the second valve 118 are placed in the second position such that air flows through the renewal loop as previously discussed herein. The renewal unit 120 can be activated (e.g., turned on) such that the renewal unit 120 emits energy. The emitted energy eliminates and/or releases trapped contaminants from the filter 104 during the renewal process. The treatment unit 122 treats the contaminants released from the filter 104 during the renewal process. The treatment unit 122 treats contaminants released from the filter 104 by entrapping, oxidizing, reducing, inactivating, degrading, or filtering the contaminants. In some embodiments, the treatment unit 122 is configured for treating, e.g., entrapping, oxidizing, reducing, or adsorbing gas phase contaminants in the air stream and/or contaminants vaporized from the filter 104, e.g., during the renewal process. After the renewal process is complete (e.g., after a period of time has passed) the renewal unit 120 can be deactivated (e.g., turned off), and the valves 116 and 118 can be returned to their first position allowing air to be treated by the air purification system 100 as previously discussed herein.

The renewal process may include supplying energy (e.g., heat) directly to the filter 104, heating the air and recirculating the heated air through the filter 104, and/or deactivating trapped contaminants with energy supplied by the renewal unit 120 (e.g., catalytic oxidation/reduction, thermal inactivation of pathogens). Filter renewal can renew filter function, increase the filtration efficiency, sanitize filter, and reduce the pressure drop. The renewal of the filter can advantageously prolong the time interval between filter replacements.

In some embodiments, the renewal unit 120 includes a heat source, which can be employed to raise the temperature of the filter during the renewal process to an elevated temperature in a range, for example, between about 25° C. and about 750° C. For example, the temperature range for the renewal process can be between about 50° C. and about 400° C., or about 60° C. and about 300° C. A heat source may include, but is not limited to, a resistive heater (e.g., a bobbin heater, a heating coil, a heat tape, an inductive coil, a flame, or sources of electromagnetic emission, e.g., in the form of light (e.g., infrared radiation), or magnetic field, a radiative heater, an inductive heater, etc.). The heat source may include a heat exchanger or another type of heat recovery device.

In some embodiments, the renewal unit 120 emits UV light. In other embodiments, the renewal unit 120 may emit a burst of pressurized air that frees contaminants captured by the filter 104. In this embodiment, the burst of pressurized air is applied to the filter in a direction that is opposite to the direction of the flow of the air to be filtered.

Figure 1D:
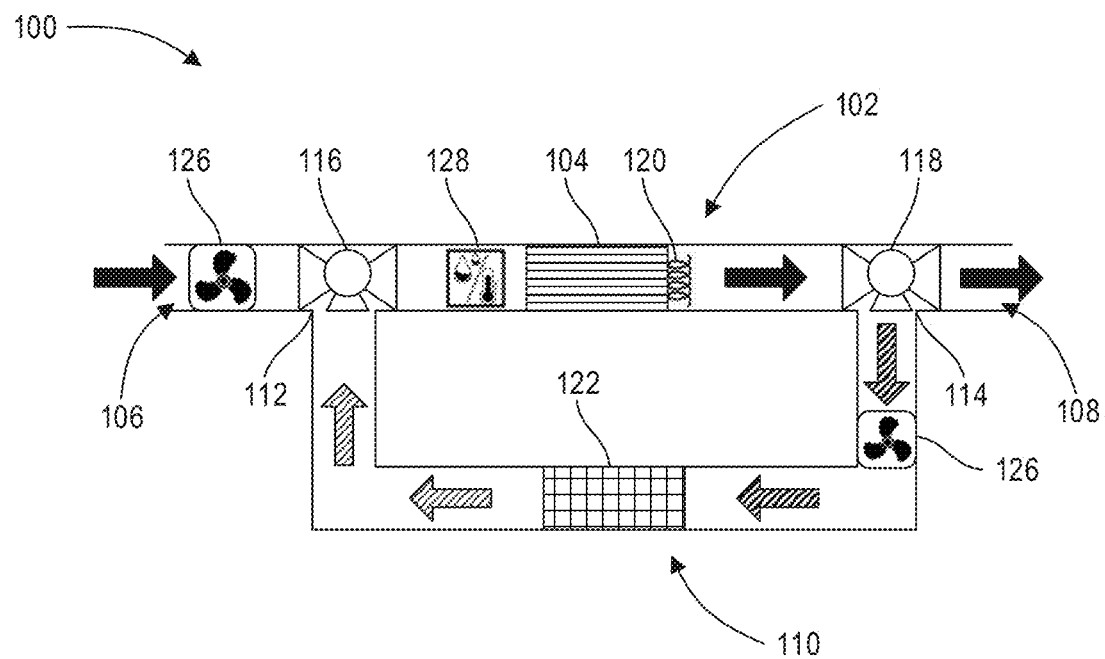

While FIG. 1A depicts the renewal unit 120 as disposed within the primary conduit 102, in other embodiments (FIG. 1B) the renewal unit 120 may be located elsewhere within the air purification system 100 (e.g., disposed within the secondary conduit 110). In embodiments wherein the renewal unit 120 directly supplies energy to the filter 104, the renewal unit 120 may be physically coupled to the filter 104. For example, in some such embodiments, the filter and the renewal unit may be disposed in a single housing to provide an integrated unit. In one embodiment, the renewal unit 120 is positioned upstream from the filter 104 (FIG. 1C) and in another embodiment, the renewal unit 120 is positioned downstream from the filter 104 (FIG. 1D).

Figure 1E:
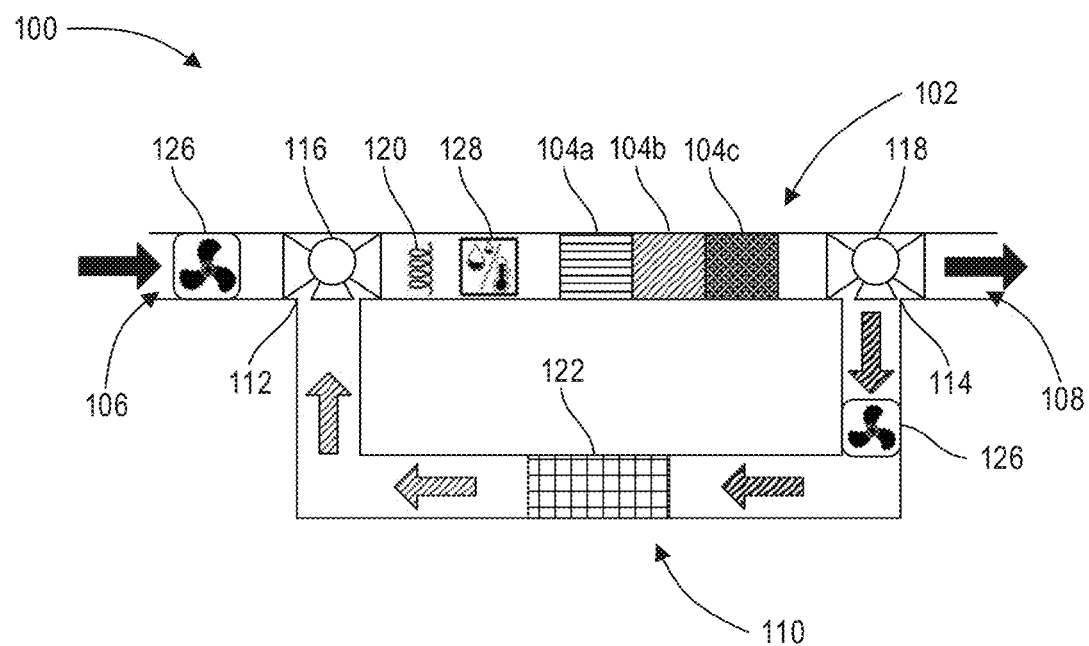

With reference to FIG. 1E, in some embodiments, the filter 104 may include one or more of a filter element 104*a* (e.g., a particulate filter, sorption filter, etc.), a heat transfer element(s) 104*b*, and a catalytic element 104*c* (e.g., thermal catalyst, biocatalyst, photocatalyst, etc.) In some embodiments, the catalyst is coated on a substrate of the filter 104. The heat transfer element 104*b* is positioned along a path of air flow. The heat transfer element 104*b* increases thermal contact with the flowing air and is configured to improve heat dissipation and/or ab sorption efficiency.

As depicted in FIGS. 1A-1J, the air purification system 100 may include fans 126 disposed in the primary conduit 102 and the secondary conduit 110. The fans 126 facilitate the passage of the air through the air purification system 100. While FIGS. 1A-1J depict the air purification system 100 as including two fans 126, the air purification system 100 may include more or less fans 126 (e.g., 1, 2, 5, etc.). Furthermore, while FIGS. 1A-1J depict a fan 126 within the primary conduit 102 that is positioned upstream from the first valve 116 and a fan 126 within the secondary conduit 110 that is positioned upstream from the treatment unit 122 other embodiments, a fan 126 may be placed in other locations (e.g., in the primary conduit 102 downstream from the filter 104, or in the secondary conduit 110 downstream from the treatment unit 122). During the renewal process, a fan 126 that is located in the secondary conduit 110 may be turned on such that heated air may be recirculated through the filter 104 to facilitate renewal of the filter 104.

While FIGS. 1A-1J depict the fans 126 as creating a clockwise flow direction within the renewal loop, in other embodiments, one or more of the fan(s) 126 disposed within the renewal loop may be configured to establish an air flow in a counterclockwise direction within the renewal loop during renewal. In some embodiments, air flow moving in a counterclockwise direction may release contaminants stored on the filter 104 thereby renewing the filter 104.

In other embodiments, air flow through the air purification system 100 can be accomplished via an external element, e.g., a pump or a blower, associated with another system to which the air purification system can be coupled (e.g., an HVAC system).

Figure 1F:
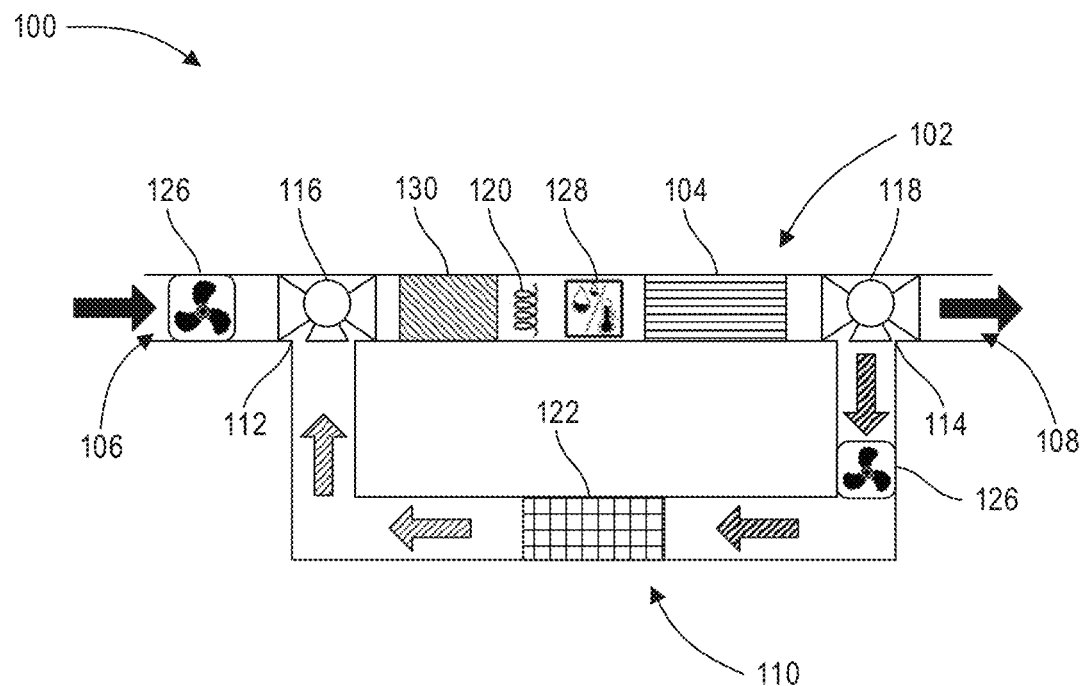
Figure 1G:
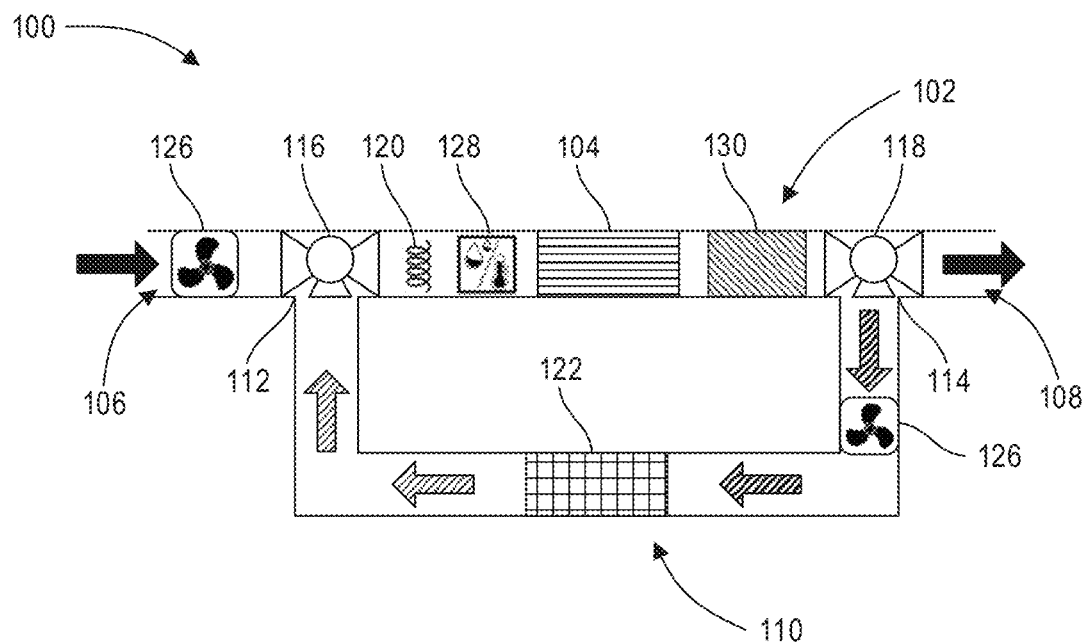

With particular reference to FIGS. 1F and 1G, in some embodiments the air purification system 100 includes another filter 130. In some embodiments, the filter 130 may be any type of filter described herein including a combination of filters described herein. In some embodiments, on the other hand, they may be of different types. In a particular embodiment, the filter 130 may be a sorption filter. As depicted in FIG. 1F, in one embodiment the filter 130 may be disposed in the primary conduit 102 upstream from the filter 104 and as depicted in FIG. 1G, in another embodiment, the filter 130 may be disposed in the primary conduit 102 downstream from the filter 104. While FIGS. 1F and 1G depict the filter 130 as disposed within the primary conduit 102 in other embodiments, the filter 130 may be disposed within the secondary conduit 110.

The air purification system 100 may also include a sensor 128. The sensor 128 may include, but is not limited to, temperature, humidity, pressure, particulate, VOC, $CO_2$, or other sensors. In some embodiments, the sensor 128 may include a light or sound detector. In these embodiments, the sensor 128 may be disposed within an enclosed environment (e.g., the enclosed environment 131 depicted in FIGS. 1H and 1I). While FIGS. 1A-1J depict the air purification system 100 as including one sensor 128, in some embodiments the air purification system 100 includes a plurality of sensors 128. In these embodiments, each of the plurality of sensors 128 may be the same or different.

In some embodiments, the sensor 128 may be used to monitor one or more environmental factors to enable environmental triggering of a renewal operation or starting or modulating the system for air purification operation. For example, the sensor 128 may monitor the temperature, the concentration of contaminants in the air, the noise level, the back pressure, etc.

Figure 1H:
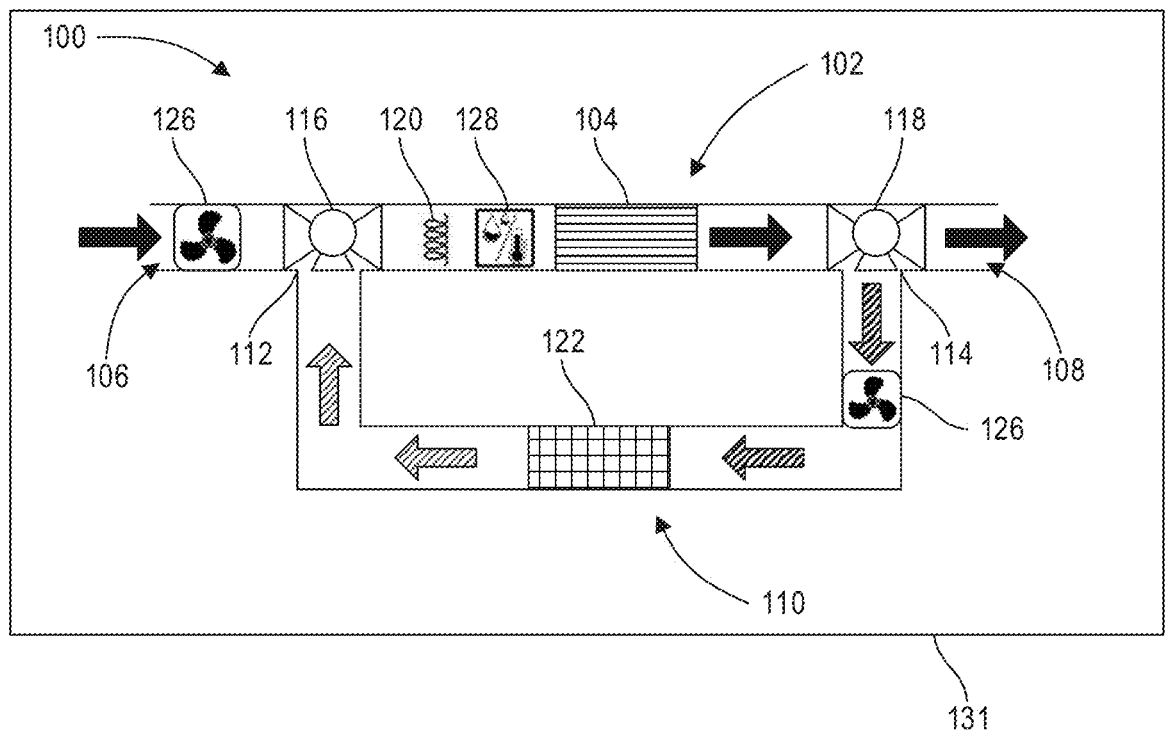
Figure 1I:
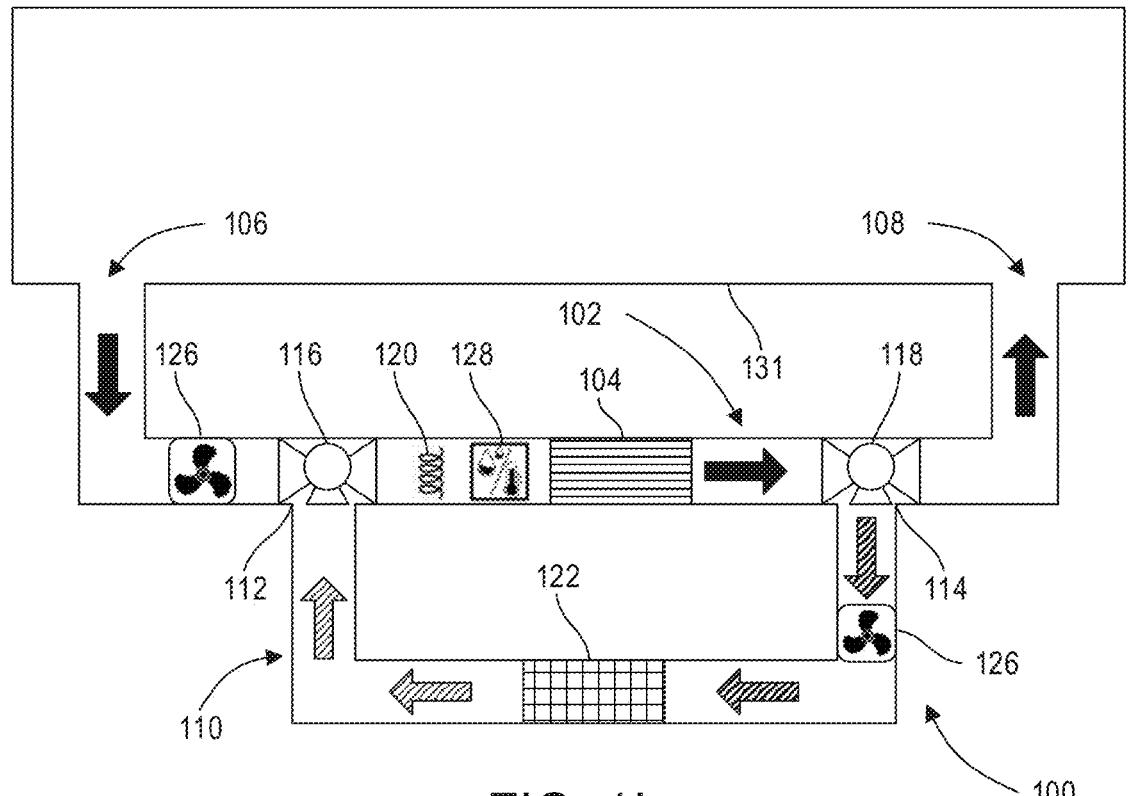

As depicted in FIGS. 1H and 1I, the air purification system 100 may be within or in fluid communication with an enclosed environment 131 (e.g., a vehicle cabin, aircraft cabin, a room, a building, etc.) such that the air from within the enclosed environment 131 is treated and recirculated back into the enclosed environment 131 by the air purification system 100. In these embodiments, the inlet 106 and the outlet 108 are in fluid communication with the enclosed environment 131. Ambient air from the enclosed environment 131 enters the conduit 102 via the inlet 106, passes through the filter 104 and exits the conduit 102 via the outlet 108 as treated air, and reenters the enclosed environment 131. In some such embodiments, the air purification system may include a treatment unit that can treat, e.g., decompose, inactivate, or eliminate, the contaminants or their remnants that are released from the filter during a renewal period so as to ensure that the renewal of the filter does not cause entry of pollutants into the environment.

In one embodiment (FIG. 1H) the entire air purification system 100 (including the conduits 102 and 110) are disposed within the enclosed environment 131. In another embodiment (FIG. 1I), the conduits 102 and 110 are external from the enclosed environment 131, but are in fluid communication with the enclosed environment.

Figure 1J:
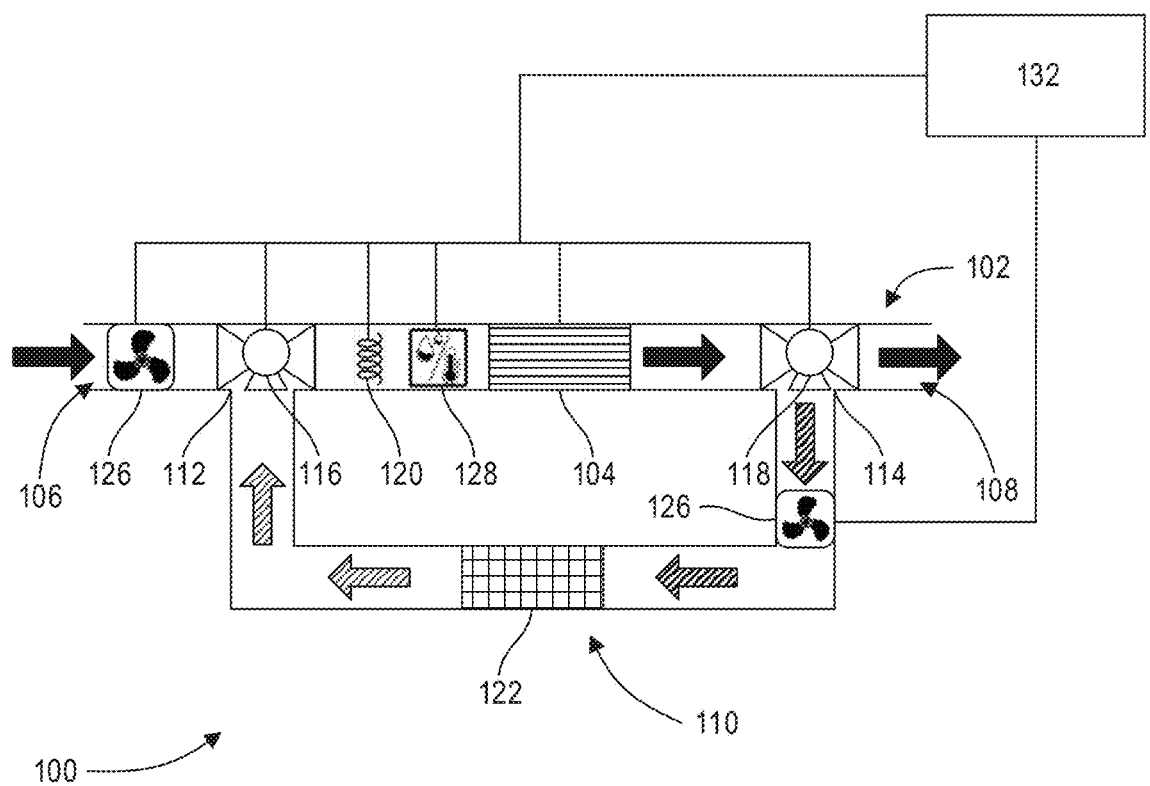

With reference to FIG. 1J, the air purification system 100 may further include a controller 132, which is in communication with the valves 116 and 118, the renewal unit 120 and the fan(s) 126, and the sensor 128 via a wired or wireless connection.

The controller is configured to move the valves 116 and 118 between the first and second positions, activate (e.g., turn on) and deactivate (e.g., turn off) the renewal unit 120 and the fans 126. Stated another way, the controller 132 is configured to initiate the renewal process. In one embodiment, the controller 132 is configured to initiate the renewal process based on a predefined schedule, e.g., on a daily, weekly, or monthly basis. In another embodiment, the controller 132 is configured to initiate the renewal process based on a user input in real time. In some other embodiments, the controller 132 may initiate the renewal process after detecting from sensor data that the accumulation of contaminants in the filter has reached a threshold. The detection may be based on different factors, such as, a pressure drop greater than an expected pressure drop across the filter, detection of contaminants released from the filter, absorption of visible or invisible parts of light spectrum by the filter, etc.

The controller 132 may operate the fans 126 independent of the renewal process to promote air flow through the conduits 102 and 110.

Furthermore, the controller 132 receives one or more signals from the sensor 128 that is indicative of a parameter measured by the sensor 128 (e.g., temperature, pressure, etc.). The controller 132 may modify an operation of the air purification system 100 (e.g., start or stop renewal, increase or decrease fan speed, modify valve positions, etc.) based on the received signal. For example, the controller 132 may initiate a renewal process when a back pressure measured by the sensor 128 exceeds a threshold. In another example, the controller 132 may initiate a renewal process when an accumulation of contaminants in the filter 104 exceeds a threshold. The controller may determine the threshold has been exceeded based on a pressure drop (as measured by the sensor 128) is greater than an expected pressure drop across the filter, a detection of contaminants released from the filter 104, absorption of visible or invisible parts of light spectrum by the filter, etc.

Referring now to FIGS. 2A-2K, an air purification system 200 is shown in accordance with an exemplary embodiment. Unlike the air purification system 100, the air purification system 200 has a substantially linear configuration and does not include a secondary conduit. The air purification system 200 may be used outdoors or indoors (e.g., in a building, a vehicle cabin, an aircraft cabin, or other enclosed environments).

The air purification system 200 includes a conduit 202 and a filter 204 disposed within the conduit 202. The conduit 202 extends between an inlet 206 and an outlet 208. In some embodiments, the filter 204 is configured to treat contaminant matter, to inactivate, reduce, and preferably remove contaminants, such as viruses and gaseous contaminants, e.g., VOCs, from the passing air via catalytic processes, e.g., such as oxidation or reduction. In some embodiments, the filter 204 may be a functionalized filter.

During operation of the air purification system 200, ambient air enters the air purification system 200 via the inlet 206, is treated by the filter 204 thereby generating "treated air" and the treated air exits the air purification system 200 via the outlet 208.

Figure 2A:
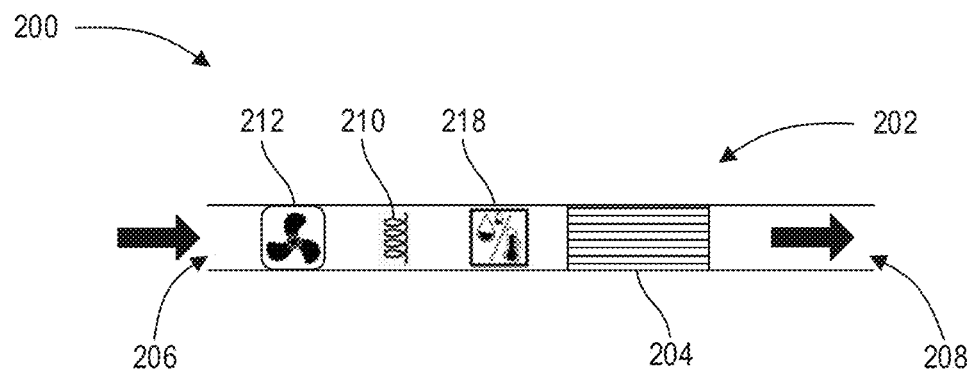
FIGS. 2A-2K are schematic representations of various single conduit air purification systems according to various exemplary embodiments.
Figure 2B:
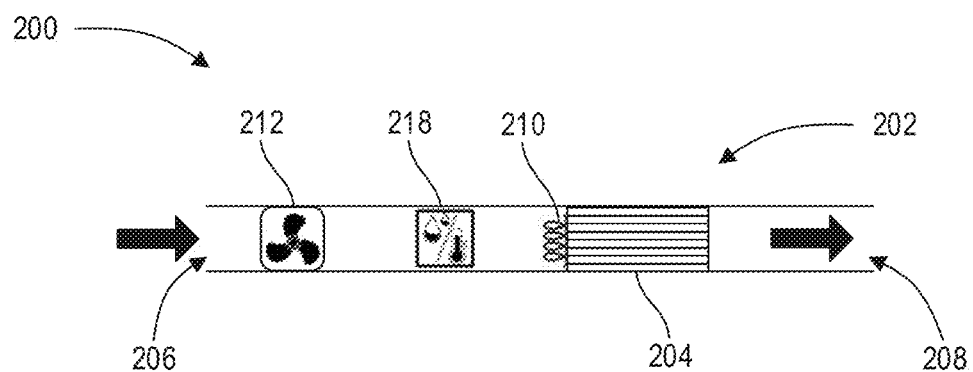
Figure 2C:
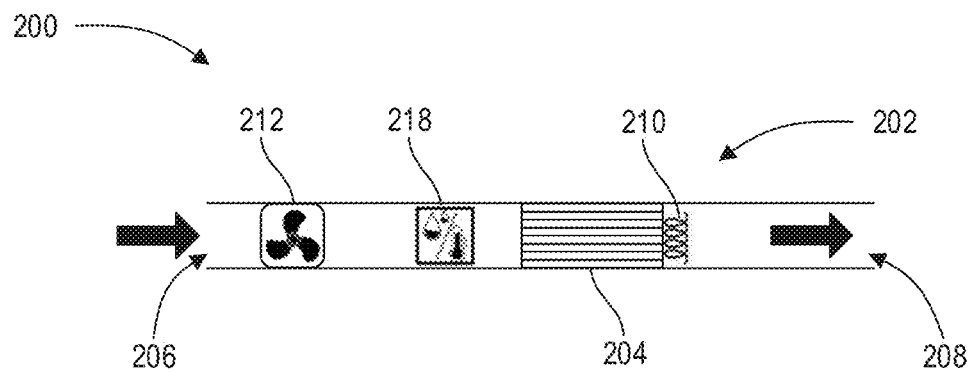

The air purification system 200 includes a renewal unit 210. When activated (e.g., turned on), the renewal unit 210 emits energy that eliminates and/or releases trapped contaminants from the filter 204 during the renewal process. The renewal unit 210 may be similar to the renewal unit 120. In some embodiments (FIGS. 2B and 2C), the renewal unit 210 is directly coupled to the filter 204. In some embodiments, the renewal unit 210 may be positioned upstream from the filter 204 (FIG. 2B) and in some embodiments, the renewal unit 210 may be positioned downstream from the filter 204 (FIG. 2C).

Figure 2D:
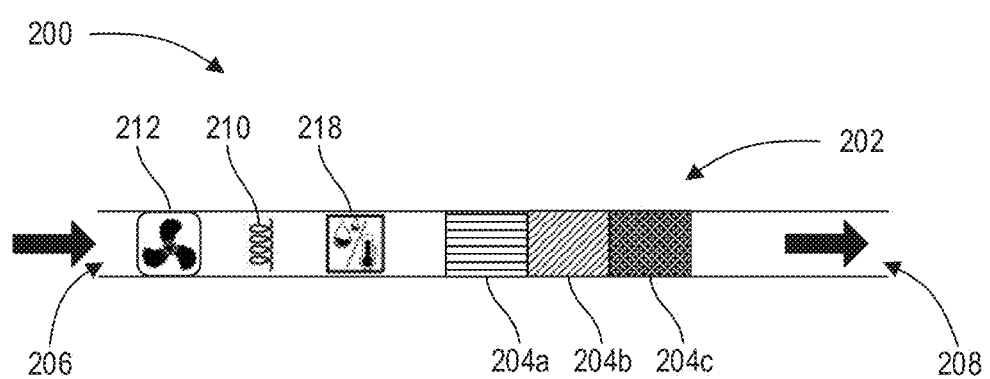

With reference to FIG. 2D, in some embodiments, the filter 204 may include one or more of a filter element 204a (e.g., a particulate filter, a sorption filter, etc.), a heat transfer element(s) 204b, and a catalytic element 204c (e.g., thermal catalyst, biocatalyst, photocatalyst, etc.). In some embodiments, the catalyst is coated on a substrate of the filter 204. The heat transfer element 204b is positioned along a path of air flow. The heat transfer element 204b increases thermal contact with the flowing air and is configured to improve heat dissipation and/or ab sorption efficiency.

The air purification system 200 may further include a fan 212 for driving air through the conduit 202. In other embodiments, air flow channeled through the air purification system 200 can be accomplished via an external element as previously discussed herein with respect to the air purification system 200.

Figure 2E:
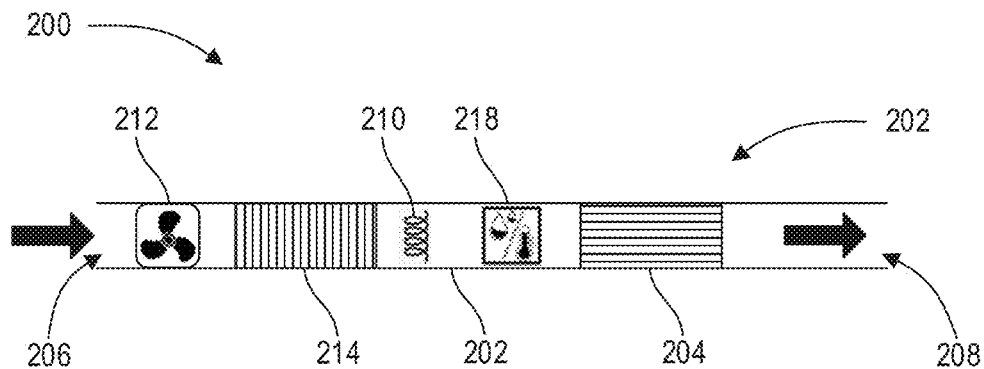
Figure 2F:
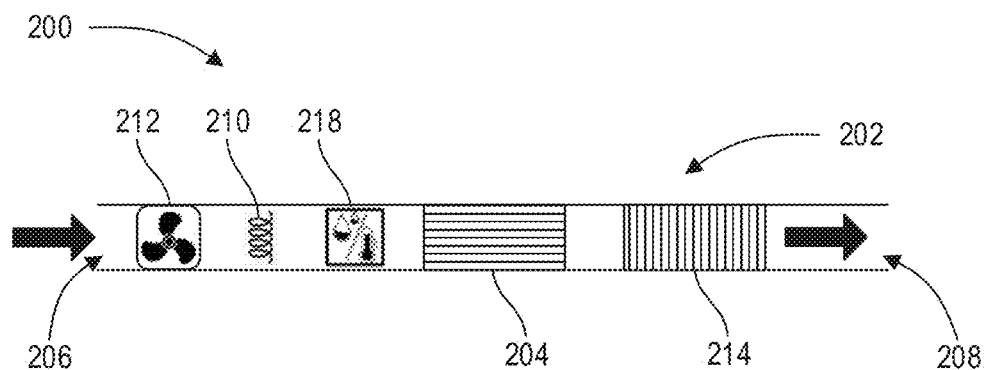
Figure 2G:
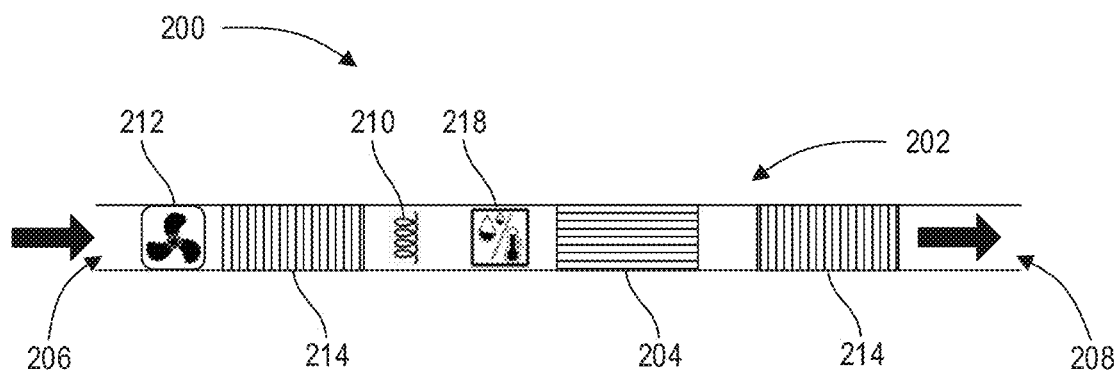
Figure 2H:
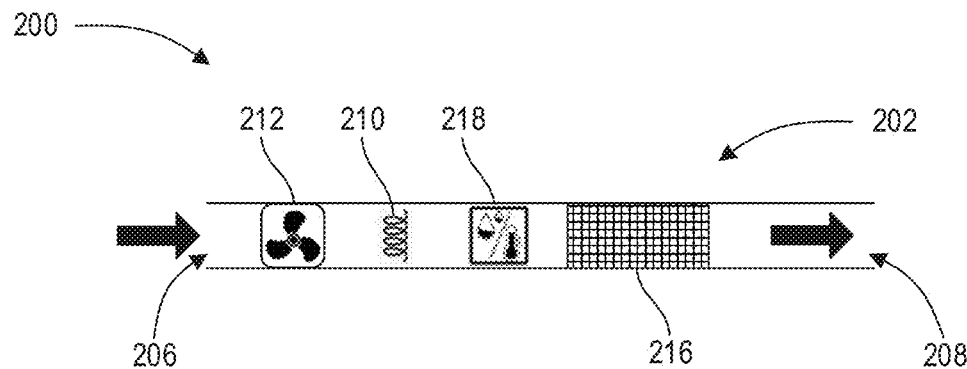

Referring now to FIGS. 2E-2H, the air purification system 200 may further include a treatment unit 214 disposed within the conduit 202. The treatment unit 214 may be similar to the renewal unit 110. In one embodiment, the treatment unit 214 is disposed upstream from the filter 204 (FIG. 2E) and in another embodiment, the treatment unit 214 is disposed downstream from the filter 204 (FIG. 2F). In some embodiments, (FIG. 2G) the air purification system 200 may include two treatment units 214. In yet another embodiment (FIG. 2H), the filter 204 and the treatment unit 214 may be included in the same filtration unit 216. The treatment unit 214 may be a sorption filter, a catalytic filter, or a combination thereof. The filter 204 may be structurally the same as the treatment unit 214 and in embodiments wherein the air purification system 200 includes a plurality of treatment units 214, each treatment unit 214 may be structurally the same or structurally different.

In some embodiments in which the direction of the air flow during the renewal process is opposite to the direction of air flow during air filtration, the treatment unit 214 is located upstream from the filter 204. and can capture contaminants released from the filter during the renewal process. In some embodiments in which the air flow during the renewal process is in the same direction as the direction of the air flow during air filtration, the treatment unit 214 is positioned downstream from the filter 204 and can treat the contaminants (or their remnants) released from the filter 204 during the renewal process. In some embodiments, the treatment unit 214 is configured for adsorbing gas phase contaminants in the air stream and/or contaminants vaporized by the filter 204.

In some embodiments, the air purification system 200 may not include the treatment unit 214 (FIG. 2A) or the treatment unit 214 may not be located downstream from the filter 204 (FIG. 2E). In some such embodiments, the renewal unit 210 and the filter 204 may be configured such that the filter 204 does not release harmful contaminants during the renewal process. For example, the air purification system may include a valve downstream from the filter 204. The valve may move between a first position, wherein air is allowed to exit the conduit 202 and a second position, wherein air is not permitted to exit the conduit 202. During renewal, the valve may be placed in a closed position such that air and any contaminants released form the filter 204 during the renewal process are not allowed to exit the conduit 202. Furthermore, in these embodiments, air flow through the conduit 202 may be reduced (e.g., by stopping fans associated with the air purification system 200) such that there is little or no air flow.

As depicted in FIGS. 2A-2K, the air purification system 200 may further include a sensor 218. The sensor 218 may include, but is not limited to, temperature, humidity, pressure, particulate, VOC, $CO_2$, or other sensors. In some embodiments, the sensor 218 may include a light or sound detector. In these embodiments, the sensor 218 may be disposed within an enclosed environment (e.g., the enclosed environment 222 depicted in FIGS. 2I and 2J). While FIGS. 2A-2K depict the air purification system 200 as including one sensor 218, in some embodiments the air purification system 200 includes a plurality of sensors 218. In these embodiments, each of the plurality of sensors 218 may be the same or different.

Figure 2I:
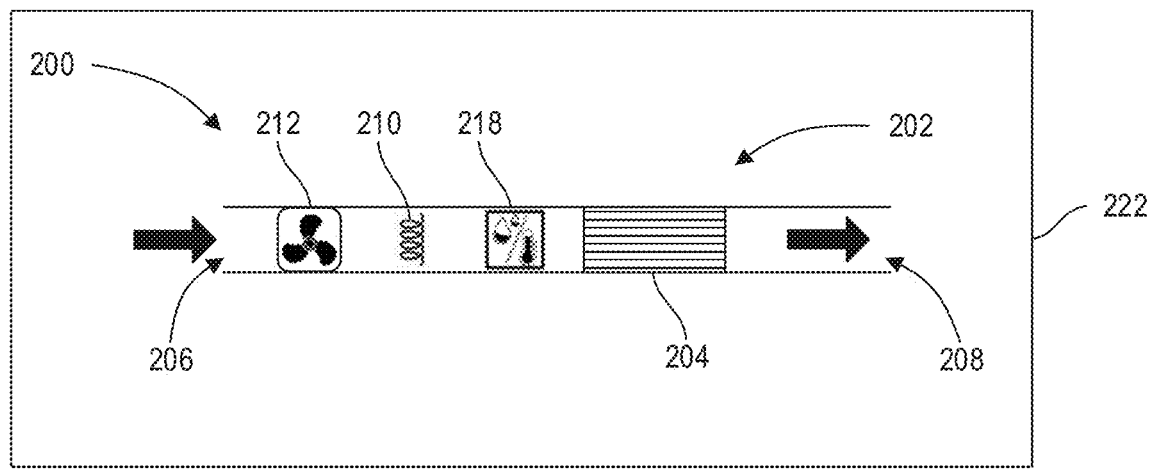
Figure 2J:
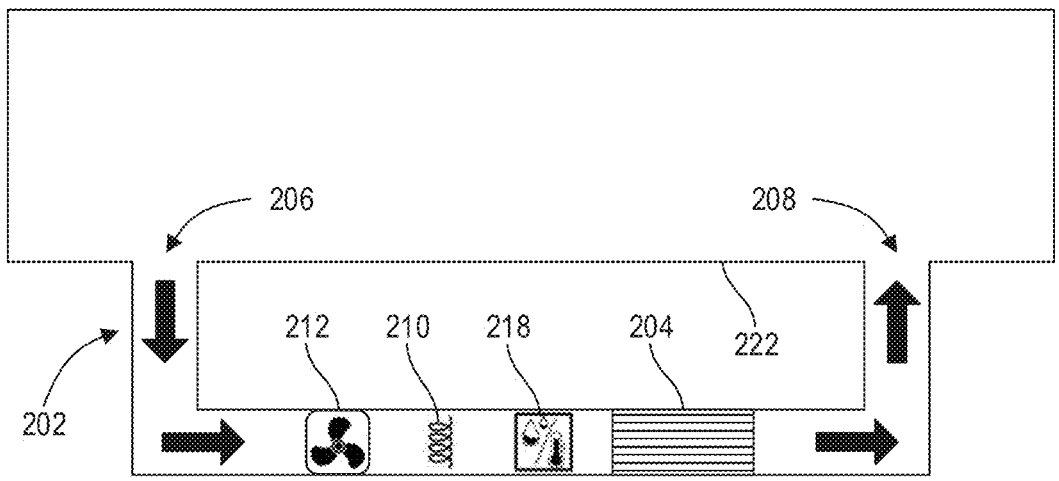

As depicted in FIGS. 2I and 2J, the air purification system 200 may be located inside an enclosed environment 222 or may be positioned external to the enclosed environment and in fluid communication with the enclosed environment 222. The enclosed environment 222 may be a vehicle cabin, aircraft cabin, a room, a building, etc. In such configurations, system 200 may treat the air from within the enclosed environment 222 and recirculate the treated air into the enclosed environment 222. In these embodiments, the inlet 206 and the outlet 208 are in fluid communication with the enclosed environment 222. Ambient air from the enclosed environment 222 enters the conduit 202 via the inlet 206, passes through the filter 204 and exits the conduit 202 via the outlet 208 as treated air, and reenters the enclosed environment 222.

Figure 2K:
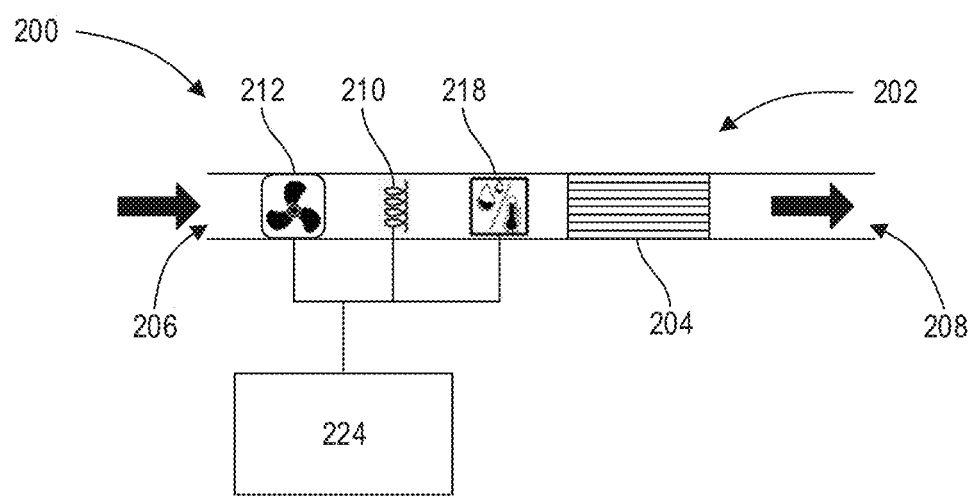

With reference to FIG. 2K, the air purification system 200 may further include a controller 224. The controller 224 is in communication with the renewal unit 210, the fan(s) 212, and the sensor 218 via a wired or wireless connection. The controller is configured to activate (e.g., turn on) and deactivate (e.g., turn off) the renewal unit 210 and the fan 212. Stated another way, the controller 224 is configured to initiate the renewal process. In one embodiment, the controller 224 is configured to initiate the renewal process based on a predefined schedule, e.g., on a daily, weekly, or monthly basis. In some other embodiments, the controller 224 may be configured to initiate the renewal process based on a user input in real time.

Furthermore, the controller 224 receives one or more signals from the sensor 218 that is indicative of a parameter measured by the sensor 218 (e.g., temperature, pressure, etc.). The controller 224 may modify an operation of the air purification system 200 (e.g., start or stop renewal, increase or decrease fan speed, modify valve positions, etc.) based on the received signal. For example, the controller 224 may end a renewal process when a back pressure measured by the sensor 218 falls below a threshold. In another example, the controller 224 may initiate a renewal process when an accumulation of contaminants in the filter 204 exceeds a threshold. The controller may determine the threshold has been exceeded based on a pressure drop (as measured by the sensor 218) that is greater than an expected pressure drop across the filter, based on a detection of contaminants released from the filter 204, or based on absorption of visible or invisible light by the filter, etc.

The controller 224 may operate the fan 212 independent of the renewal process to promote air flow through the conduit 202.

While FIGS. 1A-1J and 2A-2K depict the air purification systems 100 and 200 as having a horizontal orientation, in other embodiments, the air purification systems 100 and 200 can have an orientation that facilitates or is natural for heat transfer or flow. For example, in one embodiment, the air purification systems 100 and 200 may have a vertical orientation such that the outlets 108 and 208 are vertically above the inlets 106 and 206. In this embodiment, the renewal units 120 and 210 may emit heat and may be positioned vertically below the filters 104 and 204. As emitted heat rises, heated air passes through the filters 104 or 204 thereby renewing the filters 104 and 204. Furthermore, while FIGS. 1A-1J and 2A-2K depict the air purification systems 100 and 200 as including one renewal unit 120 or 210, in some embodiments, the air purification systems 100 and 200 may include a plurality of renewal units 120 or 210 at the locations described herein.

A variety of filters can be employed in an air purification system according to the present teachings. As discussed above, in many embodiments, the filters can have a primary porous structure that can provide filtration and a secondary porous structure that is coupled to the primary porous structure, e.g., a coating or a filler positioned in pores associated with the primary porous structure, and can modulate the filtration capability of the primary porous structure.

Figure 3A:
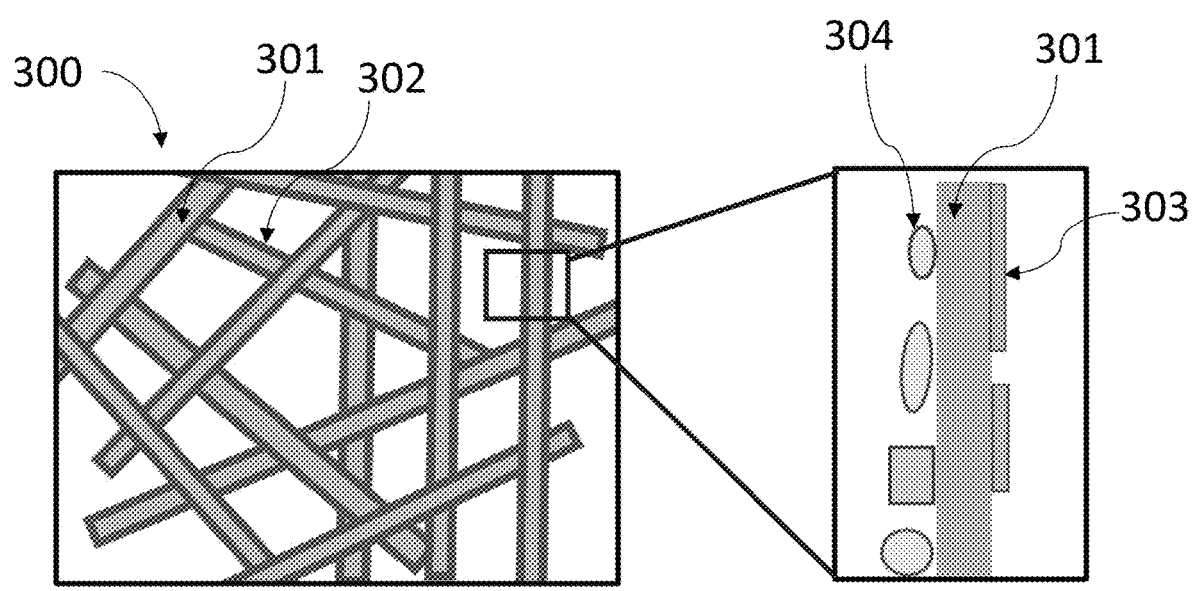
FIGS. 3A and 3B are a schematic representation of a functional/modified porous substrate of a filter in accordance with an exemplary embodiment.
Figure 3B:
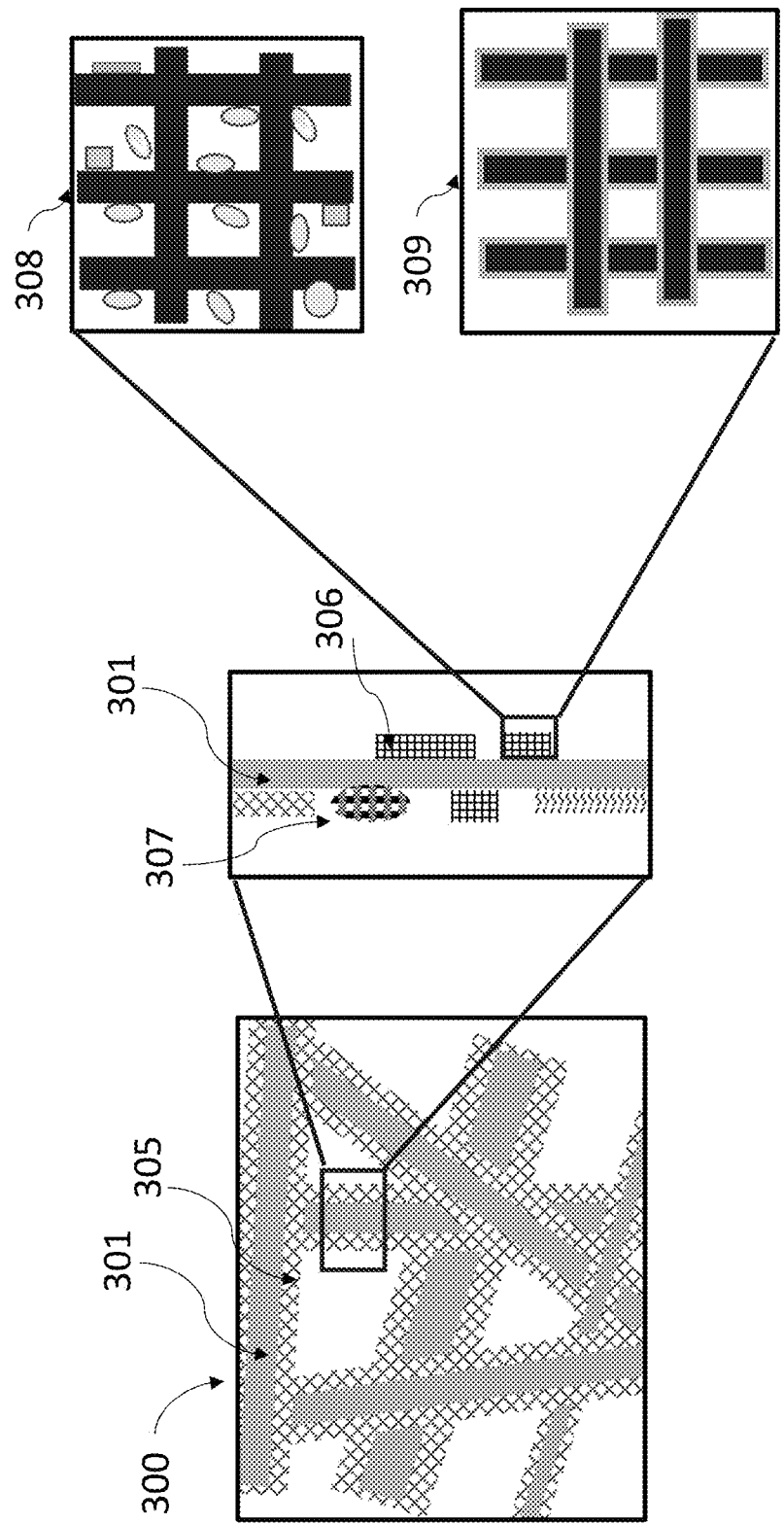

Referring now to FIG. 3A-B a structure of a functionalized filter 300 that includes a macroscopic porous substrate (e.g., fibrous filter) with various types of surface coatings in accordance with an exemplary embodiment. FIG. 3A describes a functionalized filter 300 consisting of fibrous filter media (e.g., a fiber) 301 coated with reactive medium. In some embodiments, the reactive medium includes a continuous film 302. In other embodiments, the reactive medium includes a plurality of discontinuous surface segments 303 or can comprise a plurality of nanoparticles 304 distributed within at least some portions of the filter. The nanoparticles can be 0.5 nm to 500 nm.

In some embodiments, an average cross-sectional dimension (e.g., in a plane perpendicular to the general direction of airflow) of the one or more channels of the macroscopic substrate 300 can be in a range of about 10 nm to about 3 mm. By way of example, the average cross-sectional dimension of the channels can be in a range of about 100 nm to about 5 microns, or in a range of about 10 microns to about 100 microns. In some embodiments, the one or more channels can have a length in a range of about 1 mm to about 1 m, e.g., in a range of about 100 mm to about 50 cm, or in a range of about 200 mm to about 100 cm.

In some embodiments, the reactive medium can include materials of biological origin. The biological material can include, for example, a protein that is chemically or physically coupled to a surface portion of the filter. By way of example, the protein can be an enzyme.

In some embodiments, the reactive medium can include sorption materials (e.g., activated carbon, zeolites, etc.) In further embodiments, the reactive medium can include catalytic materials.

By way of example, the catalytic material can include metal nanoparticles including platinum group metals (e.g., Pd, Pt) which become catalytically active upon heating and induce oxidative damage to the surface of a pathogen within the incoming air stream and lead to its inactivation.

In some embodiments, the reactive medium may include metals, such as gold, silver, platinum, palladium, ruthenium, rhodium, cobalt, iron, nickel, osmium, iridium, rhenium, copper, chromium, tungsten, molybdenum, vanadium, niobium, tantalum, titanium, zirconium, hafnium, bimetals, metal alloys, metal compounds, such as pnictides, hydroxides, binary and complex salts, including heteropoly acids and their derivatives or a combination thereof.

In some embodiments, the reactive medium can include metal oxides, mixed metal oxides, and/or metal sulfide; some particular examples include vanadia, silica, alumina, titania, zirconia, hafnia, nickel oxide, cobalt oxide, tin oxide, manganese oxide, magnesium oxide, noble metal oxides, platinum group metal oxides, molybdenum oxides, tungsten oxides, rhenium oxides, tantalum oxide, niobium oxide, chromium oxides, scandium, yttrium, lanthanum, thorium, uranium oxides, other rare earth oxides, or a combination thereof.

In some embodiments, the reactive medium includes semiconductor materials, such as silicon or germanium, either pure or doped with elements or compounds of group III or V elements, or a combination thereof.

In some embodiments, the reactive medium can include complex salts with alkali, alkali-earth, and group (III) metals and/or transition metal salts such as salts of nickel, copper, cobalt, manganese, magnesium, chromium, iron, platinum, tungsten, zinc, or other metals. In some embodiments, a reactive medium can include a metal cation, a metal oxide, organometallic complex or combination thereof.

In certain embodiments, the reactive medium can include one or more organometallic complexes (such as metal organic frameworks), natural materials, a protein- or polysaccharide-based material, silk fibroin, chitin, shellac, cellulose, chitosan, alginate, gelatin, or a mixture thereof, and mixtures thereof.

In some embodiments, the reactive medium can include biological materials, organic material, inorganic materials or combination thereof.

In some embodiments, the reactive medium can utilize metal oxides that promote physisorption of the bioaerosols and contaminants and their breakage.

In some embodiments, the reactive medium can include nanoparticles.

In some embodiments, the nanoparticles have compositions the same as reactive medium described above including metals, metal oxides, organic compounds, and catalytic nanoparticles.

In some embodiments, the reactive medium can be further designed to provide catalytic, photocatalytic, electrocatalytic, photonic, antimicrobial, light absorbing and/or emitting, stimuli responsiveness, adsorption, and desorption properties. The reactive medium can be introduced, for example, through physical vapor deposition, atomic layer deposition, evaporation, spattering, wet chemical modification, ion impregnation, and a combination thereof.

FIG. 3B describes a functionalized filter 300 that includes a macroscopic porous substrate (e.g., fibrous filter) modified with secondary porous structure (e.g., porous coating) 305 in accordance with an exemplary embodiment.

In some embodiments, an average cross-sectional dimension (e.g., in a plane perpendicular to the general direction of air flow) of the one or more pores of the secondary porous coating can be in a range of about 1 nm to about 10 microns. By way of example, the average cross-sectional dimension of the pores can be in a range of about 10 nm to about 150 nm, or in the range of about 200 nm to 800 nm, or in a range of about 1 micron to about 5 microns.

The secondary porous coating 305 can be deposited on a surface of the fiber 301. In some embodiments, the pores of the porous coating 305 can have an average cross-sectional dimension that is about 1 to about 200 times an average size of at least one target contaminant (e.g., particulate). By way of example, the average cross-sectional dimension of the pores can be in a range of about 1 to about 200 times, or in a range of about 1 to about 100 times, or in a range of about 1.5 to about 100 times, or in a range of about 2 to about 100 times of an average size of at least one target contaminant. In some embodiments, the pores can have an average cross-sectional dimension in a range of about 1 nm to about 10 microns, or in a range of about 50 nm to about 1 microns, or in a range of about 100 nm to about 10 microns, or in a range of about 200 nm to about 10 microns, or in a range of about 250 nm to about 5 microns, or in a range of about 50 nm to about 300 nm, or in a range of about 300 nm to about 5 microns, or in a range of about 1 micron to about 2 microns.

In implementations, the pore sizes of the porous substrate 300 and the porous coating 305 can be tuned and configured to treat the contaminants of a wider size range. For macroscopic porous substrate, porosity may be predetermined. This may include ceramic monoliths that have straight channels with a variety of channel sizes typically defined as cell density (number of channels per cross-section area). In the case of fiberglass substrate, the density of material and its porosity may be based on a desired specification. The coating's porosity may be designed and selected through a variety of techniques, e.g., templating, and/or via material selection.

In some embodiments, the porous coating 305 includes a continuous film. In other embodiments, the porous coating includes a plurality of discontinuous surface segments 306, and/or can comprise a plurality of functional porous particles 307 distributed within at least some portions of the filter. The functional porous particles can be 0.5 microns to 30 microns in size.

In other embodiments, the secondary porous coating can comprise one of silica, alumina, titania, zirconia, ceria, hafnia, vanadia, beryllia, noble metal oxides, platinum group metal oxides, titania, tin oxide, molybdenum oxide, tungsten oxide, rhenium oxide, tantalum oxide, niobium oxide, chromium oxide, scandium oxide, yttria, lanthanum oxide, thorium oxide, uranium oxide, other rare earth oxides, and a combination thereof. In some embodiments, the coating can exhibit a thickness in a range of about 0.5 to about 200 micrometers, e.g., in a range of about 10 micrometers to about 150 micrometers, or in a range of about 50 micrometers to about 100 micrometers.

In some embodiments, the secondary porous coating can comprise biogenic materials including diatomaceous earth, pollen, silica-based particles of biological origin.

In certain embodiments, the coating can include one or more organometallic complexes (such as metal organic frameworks), inorganic polymers (such as silicone), organometallic complexes, or combinations thereof, covalent, non-covalent and supramolecular polymers (such as polystyrene, polyurethane, hydrogels, and organogels), natural materials, a protein- or polysaccharide-based material, silk fibroin, chitin, shellac, cellulose, chitosan, alginate, gelatin, or a mixture thereof, and mixtures thereof.

The secondary porous coating can be designed, for example, to be catalytically active, stimuli-responsive, chemically robust, degradable, and/or exhibit specific optical, thermal, mechanical, sorption, filtration, release, and/or acoustic properties. By way of example, such coatings can include catalytically active metal oxides such as titania, copper oxide, ceria, zirconia, manganese oxide, and nickel oxide. In certain embodiments, the coating can interact with light in a way that it becomes active toward pollutant treatment (e.g., photocatalysis, photothermal catalysis, or photoelectrocatalysis). In some embodiments, the composition of the coating can be modified to provide enhanced mechanical properties and robustness by utilizing mechanically robust materials such as alumina, tungsten oxide, and metal alloys. Yet in other embodiments, the specific optical properties can be introduced through the design of porosity and pore ordering in the coating (e.g., photonic structures such as inverse opals).

In some embodiments, the activation of catalytic/functional sites can be achieved through heat and/or light activation. For example, plasmonic nanoparticles can be responsive to certain wavelengths of the electromagnetic radiation (e.g., gold nanoparticles absorb strongly at about 530 nm).

In some embodiments, the secondary porous coating can include one or more materials that facilitate/enhance the adsorption of bioaerosols, particulates, gaseous contaminants, and other pollutants. In some embodiments, such enhanced adsorption properties can be due to the presence of reactive medium such as chemical functional groups on the surface of coating (e.g., amine or thiol), and the coating composition (e.g., metal oxides, silica, zeolites, activated carbon).

In some embodiments, the secondary porous coating can exhibit sorption (both adsorption and absorption) properties including sorption of gases (e.g., VOCs, CO2, CO, ammonia and its derivatives), contaminant matter and microorganisms (e.g., pathogens, such as bacteria, viruses, etc.).

In some embodiments, the coating can exhibit both sorption and catalytic activity. For example, the coating can include one or more metal oxides with surface properties designed with increased affinity toward certain pollutants (hydroxylated surface or surface with amine functions to improve the adsorption of polar molecules such as formaldehyde, alcohol, or hydrophilic particle or combinations thereof) and elemental composition with catalytic activity toward treatment of pollutants (e.g., nickel oxide, palladium oxide, mixed metal oxides).

In some embodiments, the functionality of the coating can originate, at least partially, from the morphological features of the coating surface such as its roughness. For example, the coating surface can comprise spikes, bumps, and/or cavities in a representative size (e.g., height, length, diameter, etc.), ranging from about 1 nm to about 50 nm. In some embodiments, the functionality of the coating can originate, at least partially, from the structural features of the coating surface such as surface crystallinity, crystal grains size, and surface phase. In some embodiments, the functionality of the coating can originate, at least partially, from the combination of surface structure and composition. In some such embodiments, the surface structure and the surface composition can synergistically cooperate to provide enhanced entrapment and filtering results.

In some embodiments, the secondary porous coating can utilize metal oxides that promote physisorption of the bioaerosols and contaminants and their breakage.

In some embodiments, the secondary porous structure (e.g., a porous coating) can include a reactive medium distributed on the surface of the coating or throughout at least some of the pores.

In some embodiments, the reactive medium has a composition described above.

In some embodiments, the reactive medium can be introduced, for example, during the coating formation or through post modification of the coating.

In some embodiments, post modification can include chemical modification of the surface of porous coating with reactive medium including nanoparticles, chemical compounds, complexes through attachment of these active components via covalent bonding, ionic bonding, van der Waals bonding, and a combination thereof.

The dimensions and properties of the macroscopic substrate 300, the porous coating 305, and the reactive media 302 may be determined depending on a target contaminant that a functionalized filter described herein (e.g., filter 104, 122, 204, 214, etc.) is designed to capture and/or treat.

In many embodiments, the compositions and materials disclosed herein offer a multi-pronged mechanism for treatment of pathogens and other particles such as ultrafine particulate, PM1, PM2.5, PM10 or their mixtures. In some embodiments, this goal can be achieved via design of a structure that includes a porous macroscopic substrate with a porous coating that is deposited on the internal surfaces of at least some of the pores of the macroscopic porous substrate. Both the porous substrate and the porous coating can include nano- and/or micro-structures. In some such embodiments, the structure can include a hierarchical porosity with the substrate having primarily microstructured pores, e.g., with pore sizes greater than 1 micron and less than 3 mm.

According to the present teachings, the coating for all embodiments can be made from a variety of materials or mixtures of materials. By way of example, in some embodiments, the materials can comprise one or more metal oxides, zeolites, metals (such as gold, palladium, platinum, silver, copper, rhodium, ruthenium, rhenium, titanium, osmium, iridium, iron, cobalt, or nickel, or a combination thereof), semiconductors (such as silicon, germanium, tin, silicon doped with group III or V elements, germanium doped with group III or V elements, tin doped with group III or V elements, or a combination thereof), a metal sulfide, a metal chalcogenide, a metal nitride, a metal pnictide and a combination thereof.

In some embodiments of the present teachings, a filter can include a porous substrate including one or more channels for allowing a flow of a medium (e.g., ambient air) containing one or more contaminants. In some embodiments, the one or more channels can be implemented as interconnected pores, providing surface areas and pore structures to facilitate entrapment of the contaminants. In some embodiments, a filter can capture the contaminants primarily via physical or mechanical entrapment. In some embodiments, the filter may be configured (e.g., functionalized) so as to at least partially inactivate, decompose, and/or entrap the contaminants. In some embodiments, by tuning the pore sizes, the modification/functionalization of the filter with secondary porous material can provide more effective entrapment of the contaminants of a wider size range. In some embodiments, the modification of the filter structure can be achieved using the following steps:

1. Applying a mixture (e.g. a slurry) of secondary porous structure components (e.g. metal oxides, metal hydroxides or a collection of functional porous particles) onto an unmodified porous filter scaffold; and 2. Treating the pre-formed secondary porous structure (e.g. drying)

In some embodiments, functional porous particles for use in various embodiments of the present teachings, can be fabricated using a spray drying, drum drying, or milling method.

In some embodiments, in use, the filters can be maintained at elevated temperatures in the range of about 15° C. to about 500° C. In some embodiments, the structure can be maintained at temperatures of about 20° C., about 30° C., about 40° C., about 50° C., about 60° C., about 70° C., about 80° C., about 90° C., about 100° C., about 125° C., about 150° C., about 175° C., about 200° C., about 225° C., about 250° C., about 275° C., about 300° C., about 325° C., about 350° C., about 375° C., about 400° C., about 425° C., about 450° C., or about 475° C. Such elevated temperatures can facilitate the treatment (e.g., inactivation) of one or more pollutants due to activation of the active sites and/or thermal contact of the inner surface of the macroscopic structure and the coating.

Although some aspects have been described with reference to the embodiments of a system and/or an apparatus, the present teachings are not limited to such embodiments, and those having ordinary skill in the art will appreciate that various changes can be made to the above embodiments without departing from the scope of the invention.

What is claimed is:

1. An air treatment system comprising:
   a conduit extending between an inlet and an outlet, wherein the inlet is configured to allow entry of ambient air from an environment into the conduit and the outlet is configured to allow exit of treated air from the conduit;
   a fibrous filter disposed within the conduit and comprising a plurality of fibers for capturing particulate contaminants in the ambient air, thereby generating the treated air, wherein the capture of the plurality of particulate contaminants by the plurality of fibers over time results in an increase in a pressure differential between the inlet and the outlet; and
   a renewal unit disposed within the conduit and configured to renew the filter via transfer of energy to the filter to cause release of at least a portion of contaminants in the filter so as to reduce said pressure differential below a threshold.

2. The air treatment system of claim 1, wherein said at least a portion of contaminants released from the filter is generated in the filter by said transferred energy prior to release of said at least a portion of contaminants by at least one of oxidizing, reducing, inactivating, and degrading of at least a portion of the captured particulate contaminants.

3. The air treatment system of claim 1, wherein the filter includes a reactive medium coupled to the filter.

4. The air treatment system of claim 3, wherein the reactive medium includes at least one of an organic material, an inorganic material, a sorbent material, a catalytic material, a material of biological origin or a combination thereof.

5. The air treatment system of claim 3, wherein said reactive medium is configured to treat at least a portion of said captured particulate contaminants by at least one of oxidizing, reducing, inactivating, and degrading, thereby generating at least a portion of the contaminants to be released via the renewal unit from the filter.

6. The air treatment system of claim 3, wherein said reactive medium is configured to treat, in combination with said transferred energy, at least a portion of said captured particulate contaminants by at least one of oxidizing, reducing, inactivating, and degrading, thereby generating at least a portion of the contaminants to be released via the renewal unit from the filter.

7. The air treatment system of claim 1, wherein the filter includes a porous coating coupled to the filter.

8. The air treatment system of claim 7, wherein the porous coating includes at least one of an organic material, an inorganic material, a sorbent material, or a catalytic material, a material of biological origin, or a combination thereof.

9. The air treatment system of claim 7, wherein the porous coating includes a reactive medium.

10. The air treatment system of claim 9, wherein said reactive medium is configured to treat at least a portion of said captured particulate contaminants by at least one of oxidizing, reducing, inactivating, and degrading, thereby generating at least a portion of the contaminants to be released via the renewal unit from the filter.

11. The air treatment system of claim 9, wherein said reactive medium is configured to treat, in combination with said transferred energy, at least a portion of said captured particulate contaminants by at least one of oxidizing, reducing, inactivating, and degrading, thereby generating at least a portion of the contaminants to be released via the renewal unit from the filter.

12. The air treatment system of claim 1, wherein the transferred energy includes heat, visible light, ultraviolet (UV) light, infrared light, electromagnetic radiation, infrared radiation, a magnetic field or a combination thereof.

13. The air treatment system of claim 1, wherein the conduit is disposed within the environment.

14. The air treatment system of claim 13, wherein the environment is an enclosed environment.

15. The air treatment system of claim 1, further comprising:
    a treatment unit disposed within the conduit, wherein the treatment unit is configured to treat the contaminants released from the filter.

16. The air treatment system of claim 11, wherein the treatment unit includes a catalytic filter, a sorption filter, or a combination thereof that is configured to retain or treat the contaminants released from the filter.

17. The air treatment system of claim 1, further comprising:
    a fan disposed within the conduit and configured to facilitate air passage through the conduit.

18. The air treatment system of claim 1, further comprising: a sensor configured to determine a parameter; and
    a controller in communication with the sensor and configured to receive a signal from the sensor that is indicative of the determined parameter and is further configured to change an operational state of the air purification system based on the received signal.

19. The air treatment system of claim 1, wherein said energy comprises a burst of pressurized air.

20. The air treatment system of claim 19, wherein the renewal unit is configured to apply the burst of pressurized air to the filter in a direction opposite to direction of flow of the ambient air.

21. The air treatment system of claim 1, wherein the renewal unit is configured to provide intermittent renewal of the filter.

22. The air treatment system of claim 1, wherein the renewal unit is configured to increase a temperature of the ambient air flowing through the filter to an elevated temperature in a range of about 50° C. to about 400° C. via transfer of the energy to the filter.

23. The air treatment system of claim 1, wherein the fibrous filter includes any of woven, nonwoven and a combination of woven and nonwoven fiber-based materials.

24. The air treatment system of claim 1, wherein said particulate contaminants have a size of equal to or less than about 10 microns.

25. The air treatment system of claim 1, wherein said renewal unit is configured to renew the filter while a flow of air is maintained within the filter.

26. The air treatment system of claim 25, further comprising a valve coupled to the outlet of the conduit for preventing the air from exiting the conduit during operation of the renewal unit.

27. The air treatment system of claim 26, further comprising a controller for controlling the renewal unit to adjust the energy transferred by the renewal unit to the filter.

28. The air treatment system of claim 1, wherein the renewal unit is configured to transfer the energy to the filter so as to raise temperature of any of air flowing through the filter and the filter to an elevated temperature in a range of about 150° C. to about 400° C.

29. The air treatment system of claim 28, wherein said elevated temperature is in a range of about 200° C. to about 400° C.

30. The air treatment system of claim 1, further comprising a catalyst for retaining or treating the contaminants released from the filter.

31. The air treatment system of claim 30, wherein the catalyst is coated on a substrate of the fibrous filter.

32. The air treatment system of claim 30, wherein the catalyst is positioned downstream from the filter.

33. The air treatment system of claim 1, wherein said fibrous filter comprises any of a high efficiency particulate air (HEPA) filter and an ultra-low particulate air (ULPA) filter.

34. An air treatment system comprising:
a primary conduit extending between an inlet and an outlet, wherein the inlet is configured to allow entry of ambient air from an environment into the primary conduit and the outlet is configured to allow treated air to exit the primary conduit;
a secondary conduit in fluid communication with the primary conduit;
a fibrous filter disposed within the primary conduit or the secondary conduit and comprising a plurality of fibers for capturing particulate contaminants in the ambient air, thereby generating the treated air; wherein the capture of the plurality of particulate contaminants by the plurality of fibers over time results in an increase in a pressure differential between the inlet and the outlet
a renewal unit disposed within the primary conduit or the secondary conduit and configured to renew the filter via transfer of energy to the filter to cause release of at least a portion of contaminants in the filter so as to reduce said pressure differential below a threshold, and
a treatment unit disposed in the secondary conduit for any of retaining and treating said at least a portion of contaminants released from the fibrous filter.

35. The air treatment system of claim 34, wherein said at least a portion of contaminants released from the filter is generated in the filter by said transferred energy prior to release of said at least a portion of contaminants by at least one of oxidizing, reducing, inactivating, and degrading at least a portion of the captured particulate contaminants.

36. The air treatment system of claim 34, wherein the filter includes a reactive medium coupled to the filter.

37. The air treatment system of claim 36, wherein the reactive medium includes at least one of an organic material, an inorganic material, a sorbent material, a catalytic material, a material of biological origin, or a combination thereof.

38. The air treatment system of claim 36, wherein said reactive medium is configured to treat at least a portion of said captured particulate contaminants by at least one of oxidizing, reducing, inactivating, and degrading, thereby generating at least a portion of the contaminants to be released via the renewal unit from the filter.

39. The air treatment system of claim 36, wherein said reactive medium is configured to treat, in combination with said transferred energy, at least a portion of said captured particulate contaminants by at least one of oxidizing, reducing, inactivating, and degrading, thereby generating at least a portion of the contaminants to be released via the renewal unit from the filter.

40. The air treatment system of claim 34, wherein the filter includes a porous coating coupled to the filter.

41. The air treatment system of claim 40, wherein the porous coating includes at least one of an organic material, an inorganic material, a sorbent material, a catalytic material, a material of biological origin, or a combination thereof.

42. The air treatment of claim 40, wherein the porous coating includes a reactive medium.

43. The air treatment system of claim 34, wherein the transferred energy includes heat, visible light, UV light, infrared light, electromagnetic radiation, infrared radiation, a magnetic field, or a combination thereof.

44. The air treatment system of claim 34, wherein the treatment unit includes a catalytic filter, or a sorption filter, or a combination thereof that is configured to retain or treat contaminants released from the filter.

45. The air treatment system of claim 34, further comprising:
a fan disposed within the primary or the secondary conduit and configured to facilitate air passage through the conduit.

46. The air treatment system of claim 34, wherein the primary and secondary conduits are within the environment.

47. The air treatment system of claim 46, wherein the environment is an enclosed environment.

48. The air treatment system of claim 34, further comprising:
a sensor configured to determine a parameter; and
a controller in communication with the sensor and configured to receive a signal from the sensor that is indicative of the determined parameter and is further configured to cause activation of the renewal unit in response to a predefined variation of said determined parameter.

49. The air treatment system of claim 48, wherein the sensor is configured to measure a pressure differential between said inlet and said outlet and the controller is configured to activate the renewal unit when said measured pressure differential exceeds a threshold.

50. The air treatment system of claim 48, wherein said parameter includes an environmental parameter.

51. The air treatment system of claim 48, wherein said parameter includes a back pressure across the fibrous filter.

52. The air treatment system of claim 34, wherein said energy comprises a burst of pressurized air.

53. The air treatment system of claim 52, wherein the renewal unit is configured to apply the burst of pressurized air to the filter in a direction opposite to direction of flow of the ambient air.

54. The air treatment system of claim 34, wherein the renewal unit is configured to increase a temperature of the ambient air flowing through the filter to an elevated temperature in a range of about 150° C. to about 400° C. via transfer of the energy to the filter.

55. The air treatment system of claim 34, wherein the fibrous filter includes any of woven, nonwoven and a combination of woven and nonwoven fiber-based materials.

56. An air treatment system comprising:
a primary conduit extending between an inlet and an outlet, wherein the inlet is configured to allow entry of ambient air from an environment into the primary conduit and the outlet is configured to allow treated air to exit the primary conduit;
a secondary conduit in fluid communication with the primary conduit;
a fibrous filter disposed within the primary conduit or the secondary conduit and configured to treat the ambient air thereby generating the treated air; and
a renewal unit disposed within the primary conduit or the secondary conduit and configured to renew the filter via transfer of energy to the filter to cause release of at least a portion of contaminants accumulated in the filter so as to substantially restore operational state of the filter,
a sensor configured to determine a parameter, a controller in communication with the sensor and configured to receive a signal from the sensor that is indicative of the determined parameter and is further configured to cause activation of the renewal unit in response to a predefined variation of said determined parameter, wherein said parameter includes an environmental parameter, and wherein said environmental parameter includes a concentration of contaminants in the ambient air.

57. The air treatment system of claim 56, wherein said change of the environmental parameter includes an increase in the concentration of the contaminants in the ambient air above a predefined threshold.

* * * * *